United States Patent
Shiota

(10) Patent No.: US 12,149,759 B2
(45) Date of Patent: Nov. 19, 2024

(54) DISPLAY CONTROL APPARATUS, DISPLAY CONTROL METHOD, AND VIDEO OUTPUT APPARATUS

(71) Applicant: Sony Group Corporation, Tokyo (JP)

(72) Inventor: Susumu Shiota, Kanagawa (JP)

(73) Assignee: Sony Group Corporation, Tokyo (JP)

( * ) Notice: Subject to any disclaimer, the term of this patent is extended or adjusted under 35 U.S.C. 154(b) by 428 days.

(21) Appl. No.: 16/635,306

(22) PCT Filed: Sep. 25, 2018

(86) PCT No.: PCT/JP2018/035510
§ 371 (c)(1),
(2) Date: Jan. 30, 2020

(87) PCT Pub. No.: WO2019/065652
PCT Pub. Date: Apr. 4, 2019

(65) Prior Publication Data
US 2020/0382823 A1    Dec. 3, 2020

(30) Foreign Application Priority Data

Sep. 26, 2017   (JP) ................................ 2017-184654

(51) Int. Cl.
*H04N 21/2343* (2011.01)
*A61B 1/00* (2006.01)
(Continued)

(52) U.S. Cl.
CPC ... *H04N 21/23439* (2013.01); *A61B 1/00009* (2013.01); *A61B 1/00016* (2013.01);
(Continued)

(58) Field of Classification Search
CPC ......... H04N 21/2662; H04N 21/23439; H04N 21/6377; H04N 21/2365; H04N 21/4316;
(Continued)

(56) References Cited

U.S. PATENT DOCUMENTS

| 9,654,739 B1 * | 5/2017 | Mitchell | .................. A61B 8/56 |
| 2003/0085999 A1 * | 5/2003 | Okamoto | ............... H04N 7/181 |
| | | | 348/E7.086 |

(Continued)

FOREIGN PATENT DOCUMENTS

| CN | 1345515 A | 4/2002 |
| CN | 101088286 A | 12/2007 |

(Continued)

OTHER PUBLICATIONS

International Search Report issued for corresponding International Application No. PCT/JP2018/035510 mailed Jan. 9, 2019.

(Continued)

*Primary Examiner* — Tan Doan
(74) *Attorney, Agent, or Firm* — Michael Best & Friedrich LLP

(57) ABSTRACT

A reception apparatus and reception method receive sub streaming concurrently with receiving main streaming. A streaming apparatus transmits sub streaming concurrently with transmitting main streaming. An operating room system includes cameras that acquire image data and an audio-visual controller that receives sub streaming from the cameras concurrently with receiving main streaming from one of the cameras. A vehicle control system includes cameras mounted onto a vehicle and an integrated unit that receives sub streaming from the cameras concurrently with receiving main streaming from one of the cameras.

22 Claims, 25 Drawing Sheets

(51) Int. Cl.
   *H04N 21/2662* (2011.01)
   *H04N 21/6377* (2011.01)
(52) U.S. Cl.
   CPC ..... *H04N 21/2662* (2013.01); *H04N 21/6377* (2013.01); *B60R 2300/406* (2013.01); *B60R 2300/60* (2013.01)
(58) Field of Classification Search
   CPC ............ H04N 21/4347; H04N 21/4621; A61B 1/00009; A61B 1/00016; B60R 1/00; B60R 2300/406; B60R 2300/60; G06V 20/56
   USPC ........................................................ 709/231
   See application file for complete search history.

(56) References Cited

U.S. PATENT DOCUMENTS

| | | | | |
|---|---|---|---|---|
| 2003/0197785 A1* | 10/2003 | White | ................ | H04N 21/2187 348/E7.086 |
| 2005/0165911 A1 | 7/2005 | Homiller | | |
| 2007/0143493 A1* | 6/2007 | Mullig | ............. | H04N 21/47202 709/232 |
| 2009/0012821 A1* | 1/2009 | Besson | ............... | H04N 21/4347 715/740 |
| 2009/0085740 A1* | 4/2009 | Klein | ................. | H04N 21/4621 348/143 |
| 2011/0057783 A1* | 3/2011 | Yagi | ....................... | G08G 1/166 348/148 |
| 2016/0099976 A1* | 4/2016 | Vargheese | ........... | H04L 65/1069 709/227 |
| 2019/0108611 A1* | 4/2019 | Izumi | ................. | H04N 21/4728 |
| 2019/0164330 A1* | 5/2019 | Sugano | ................. | G06T 19/006 |

FOREIGN PATENT DOCUMENTS

| | | |
|---|---|---|
| JP | 2016225758 A | 12/2016 |
| JP | 2017163537 A | 9/2019 |

OTHER PUBLICATIONS

Japanese Office Action dated Nov. 9, 2021 for corresponding Japanese Application No. 2017-184654.

* cited by examiner

FIG. 21
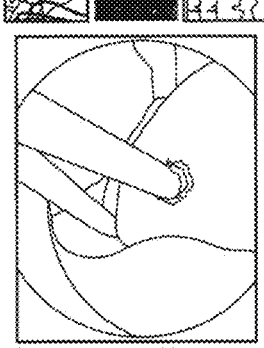
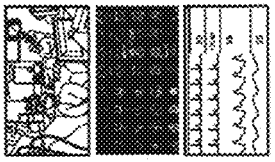
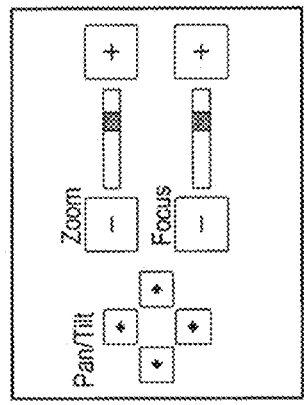
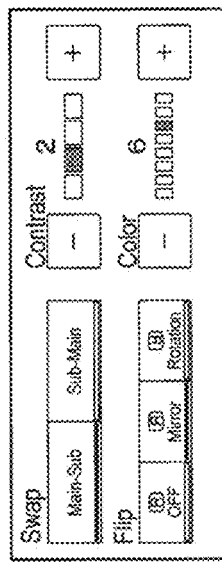
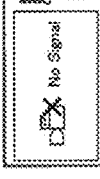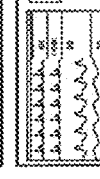

[FIG. 23]

[FIG. 25]
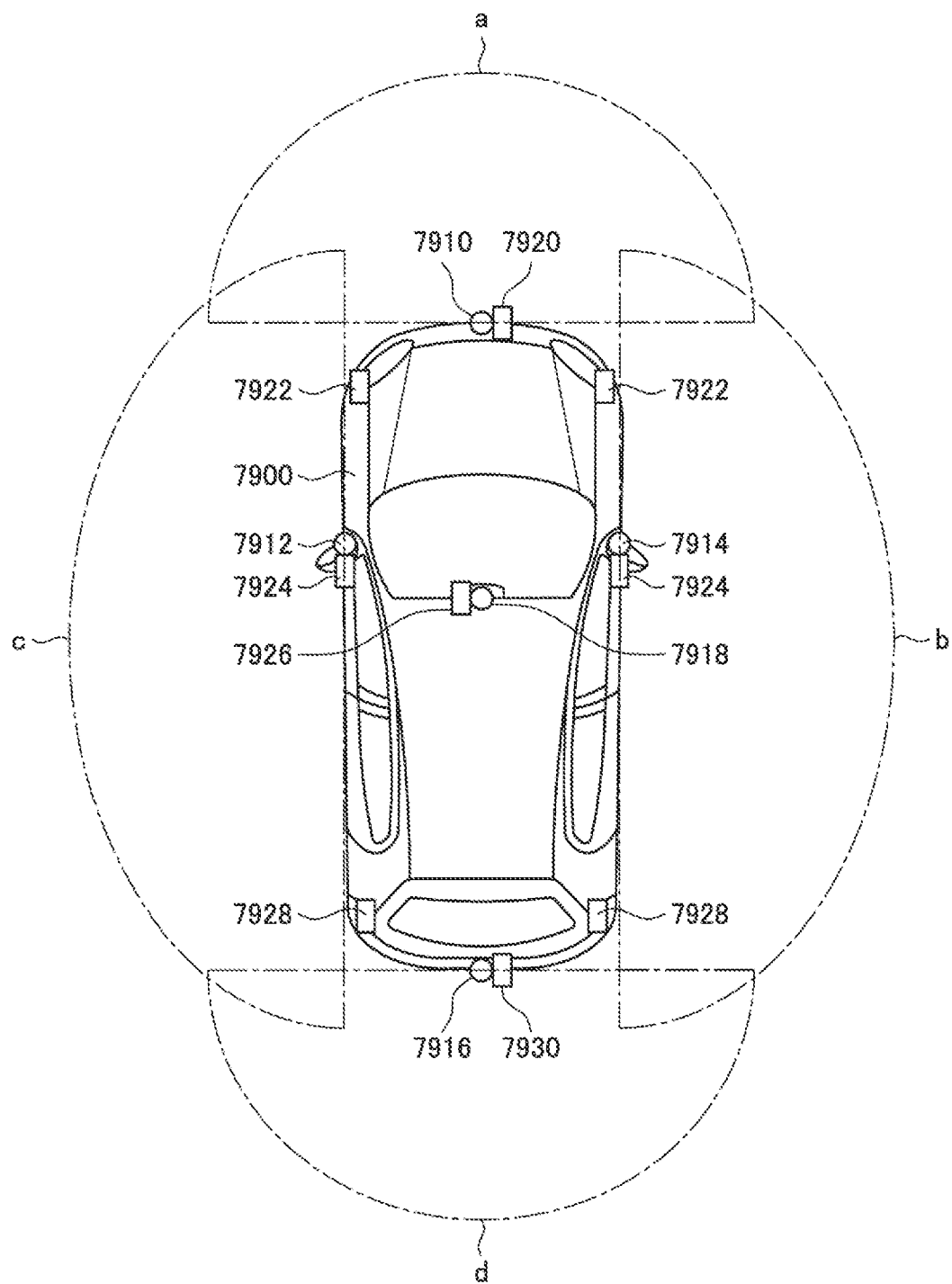

DISPLAY CONTROL APPARATUS, DISPLAY CONTROL METHOD, AND VIDEO OUTPUT APPARATUS

CROSS REFERENCE TO RELATED APPLICATIONS

This application is a National Stage Entry of Application No.: PCT/JP2018/035510, filed Sep. 25, 2018, which claims the benefit of Japanese Priority Patent Application JP 2017-184654 filed Sep. 26, 2017, the entire contents of which are incorporated herein by reference.

TECHNICAL FIELD

The present disclosure relates to a display control apparatus, a display control method, and a video output apparatus.

BACKGROUND ART

A variety of systems such as surveillance systems and broadcasting systems widely perform communication for the streaming of content including videos and sounds.

For example, PTL 1 discloses a surveillance system including a surveillance camera that generates video data of low image quality and video data of high image quality from video data obtained by performing imaging, generally transmits the streaming of the video data of low image quality, and transmits the streaming of the video data of high image quality in response to a request from the outside.

CITATION LIST

Patent Literature

[PTL 1]
JP 2008-263370A

SUMMARY

Technical Problem

However, the surveillance system described in PTL 1 selectively displays the video data of low image quality or the video data of high image quality. Therefore, it is difficult for the surveillance system described in PTL 1 to allow a user to concurrently check the video data of low image quality and the video data of high image quality whose bit rates are different. Alternatively, in the case where a display apparatus for low image quality which displays the video data of low image quality is different from a display apparatus for high image quality which displays the video data of high image quality, the display apparatus for low image quality does not display the video data of low image quality while the display apparatus for high image quality is displaying the video data of high image quality. Accordingly, it is difficult for a user to sufficiently obtain information from the display apparatus for low image quality.

The present disclosure then proposes a novel and improved display control apparatus, display control method, and video output apparatus which can concurrently display pieces of video data that are different in quality.

Solution to Problem

According to an embodiment of the present invention, a reception apparatus and reception method receive sub streaming concurrently with receiving main streaming. A streaming apparatus transmits sub streaming concurrently with transmitting main streaming.

In addition, according to the embodiment of the present invention, an operating room system includes cameras that acquire image data and an audiovisual controller that receives sub streaming from the cameras concurrently with receiving main streaming from one of the cameras.

Also according to the embodiment of the present invention, a vehicle control system includes cameras mounted onto a vehicle and an integrated unit that receives sub streaming from the cameras concurrently with receiving main streaming from one of the cameras.

Advantageous Effects of Invention

According to an embodiment of the present disclosure described above, it is possible to concurrently display pieces of video data that are different in quality. Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 21 is a diagram illustrating a display example of an operation screen in an integrated operation panel.

FIG. 25 is an explanatory diagram illustrating an example of installation positions of a vehicle outside information detecting section and an imaging section.

DESCRIPTION OF EMBODIMENTS

Figure 1:
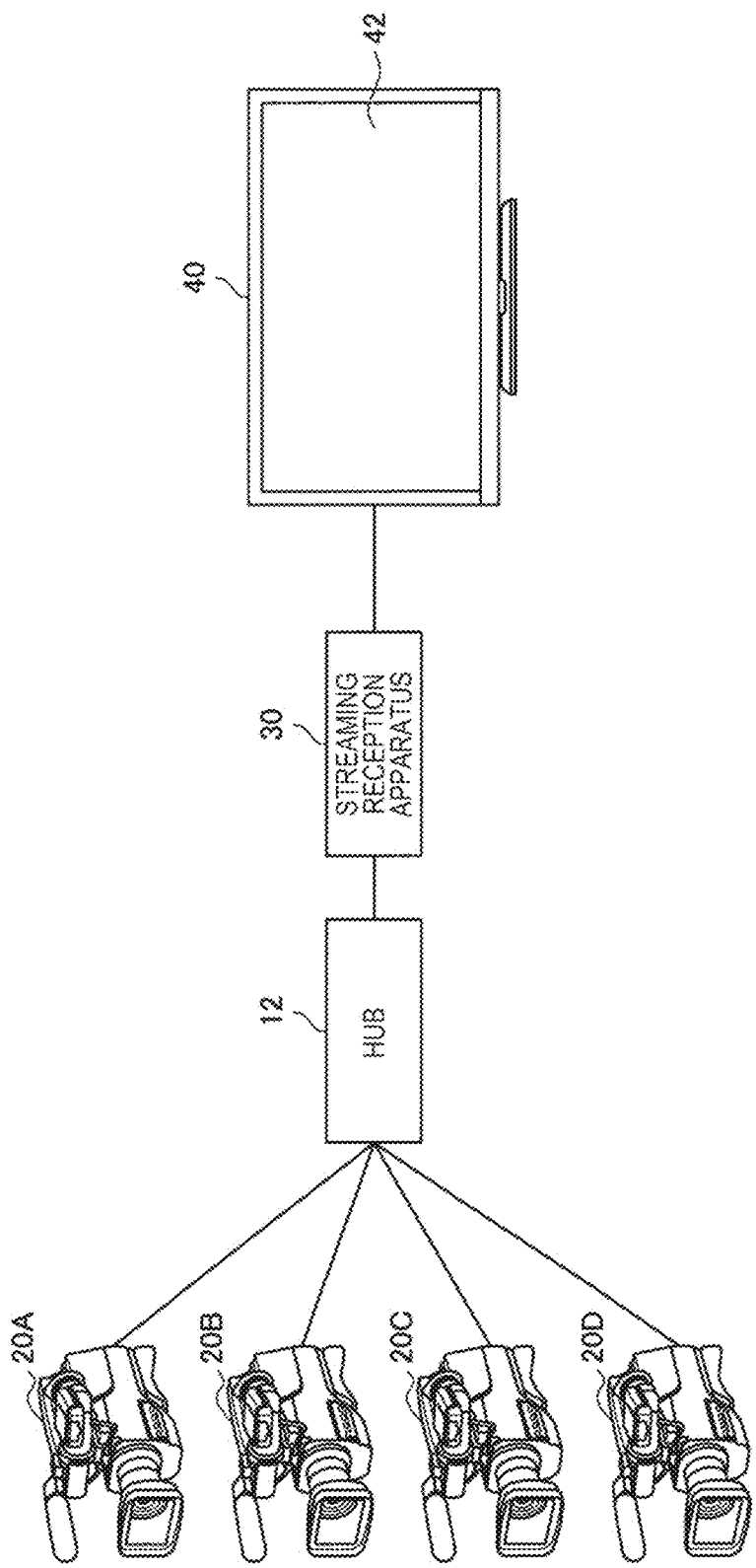
FIG. 1 is an explanatory diagram illustrating a configuration of a display control system according to an embodiment of the present disclosure.

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

Further, in the present specification and drawings, components that have substantially the same function and structure are sometimes distinguished by adding different alphabets after the same reference numeral. For example, a plurality of components with substantially the same functional component or logical meaning are distinguished like streaming transmission apparatuses 20A, 20B, and 20C as necessary. However, in the case where there is no need to particularly distinguish components that have substantially the same function and structure from each other, only the same reference sign is assigned to each of the plurality of components. For example, in the case where there is no need to particularly distinguish the streaming transmission apparatuses 20A, 20B, and 20C from each other, each streaming transmission apparatus is referred to simply as streaming transmission apparatus 20.

In addition, the present disclosure will be described in the following order.

1. Configuration of Display Control System
2. Configuration of Streaming Transmission Apparatus
3. Configuration of Streaming Reception Apparatus
4. Operation Examples
4-1. First Operation Example
4-2. Second Operation Example
4-3. Third Operation Example
5. Hardware configuration
6. Application Examples
6-1. First Application Example
6-2. Second Application Example
7. Conclusion

1. Configuration of Display Control System

An embodiment of the present disclosure relates to a display control system that performs display control which uses streaming transmitted from a plurality of streaming transmission apparatuses. The following describes the configuration of the display control system according to an embodiment of the present disclosure.

FIG. 1 is an explanatory diagram illustrating the configuration of a display control system according to an embodiment of the present disclosure. The display control system according to an embodiment of the present disclosure includes, as illustrated in FIG. 1, a plurality of streaming transmission apparatuses 20, a streaming reception apparatus 30, and a display apparatus 40. The plurality of streaming transmission apparatuses 20 are connected to the streaming reception apparatus 30 via a hub 12.

The streaming transmission apparatus 20 is an example of a video output apparatus having a function of acquiring video signals including video data, and a function of transmitting the streaming of the video signals. The streaming transmitted from each streaming transmission apparatus 20 is received by the streaming reception apparatus 30 via the hub 12. Note that the video data includes at least image data. The video data may further include sound data.

Note that, although each streaming transmission apparatus 20 is connected to the streaming reception apparatus 30 via the hub 12 in the example illustrated in FIG. 1, the streaming transmission apparatus 20 may also be directly connected to the streaming reception apparatus 30, or the streaming transmission apparatus 20 may be wirelessly connected to the streaming reception apparatus 30. In addition, the example illustrated in FIG. 1 illustrates an example in which the plurality of streaming transmission apparatuses 20 are connected to the streaming reception apparatus 30. However, one streaming transmission apparatus 20 alone may be connected to the streaming reception apparatus 30. In addition, a plurality of network interfaces may be combined, and bonding used for one communication may be used.

The streaming reception apparatus 30 receives streaming (video data) from each streaming transmission apparatus 20, and causes the display apparatus 40 to output a video on the basis of the streaming. That is, the streaming reception apparatus 30 has the function of a display control apparatus that controls the display performed by the display apparatus 40. In addition, the streaming reception apparatus 30 may have the function of a sound output control apparatus that controls the sound output made by the display apparatus 40, on the basis of the above-described streaming.

The display apparatus 40 outputs a video and a sound in accordance with the control exerted from the streaming reception apparatus 30. For example, the display apparatus 40 includes a display section 42 that displays a video supplied from the streaming reception apparatus 30. Here, with reference to FIG. 2, a specific example of a display screen of the display section 42 will be described.

Figure 2:
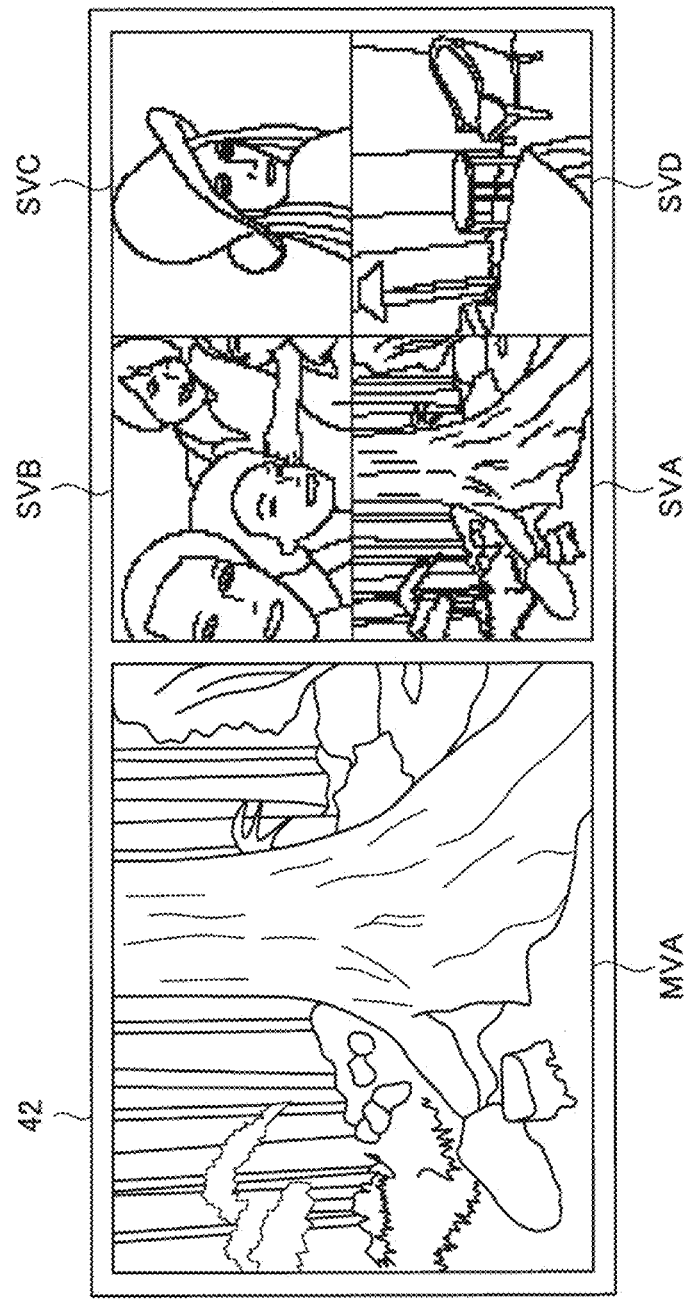
FIG. 2 is an explanatory diagram illustrating a specific example of a display screen of a display section.

FIG. 2 is an explanatory diagram illustrating a specific example of a display screen of the display section 42. In the example illustrated in FIG. 2, a display screen of the display section 42 includes one main video MVA and a plurality of sub-videos SVA to SVD. MV included in the wording main video MVA corresponds to a main video, while SV included in the wording sub-video SVA corresponds to sub-videos.

In addition, the alphabets A to D attached to the ends of the main video MVA and the sub-videos SVA to SVD represent the streaming transmission apparatuses 20 serving as transmission sources of the streaming corresponding to the videos. For example, the main video MVA and the sub-video SVA are videos based on the streaming transmitted from the streaming transmission apparatus 20A. The sub-video SVB is a video based on the streaming transmitted from the streaming transmission apparatus 20B. The sub-video SVC is a video based on the streaming transmitted from the streaming transmission apparatus 20C. The sub-video SVD is a video based on the streaming transmitted from the streaming transmission apparatus 20D.

Here, the main video is different from the sub-videos in video quality. The quality of the main video is higher than the quality of the sub-videos. That is, the main video corresponds to a high-quality video, and sub-videos correspond to low-quality videos. A user of the display apparatus 40 selects, for example, a sub-video that the user wishes to watch in detail from the plurality of sub-videos SVA to SVD, and can then cause the display section 42 to display a main video MV that expresses the selected sub-video with high quality. Note that the quality of a video is related to the resolution, the frame rate, the color difference information, and the like of the video. The bit rate of a high-quality video is higher than the bit rate of a low-quality video because of the above-described factor such as the resolution, the frame rate, or the color difference information of the video.

Note that FIG. 1 illustrates an example in which the display apparatus 40 is configured as a different entity from the streaming reception apparatus 30, but the function of the display apparatus 40 may be included in the streaming reception apparatus 30. In addition, FIG. 1 illustrates an example in which the streaming reception apparatus 30 controls one display apparatus 40, but the streaming reception apparatus 30 may control two or more display apparatuses 40.

Figure 3:
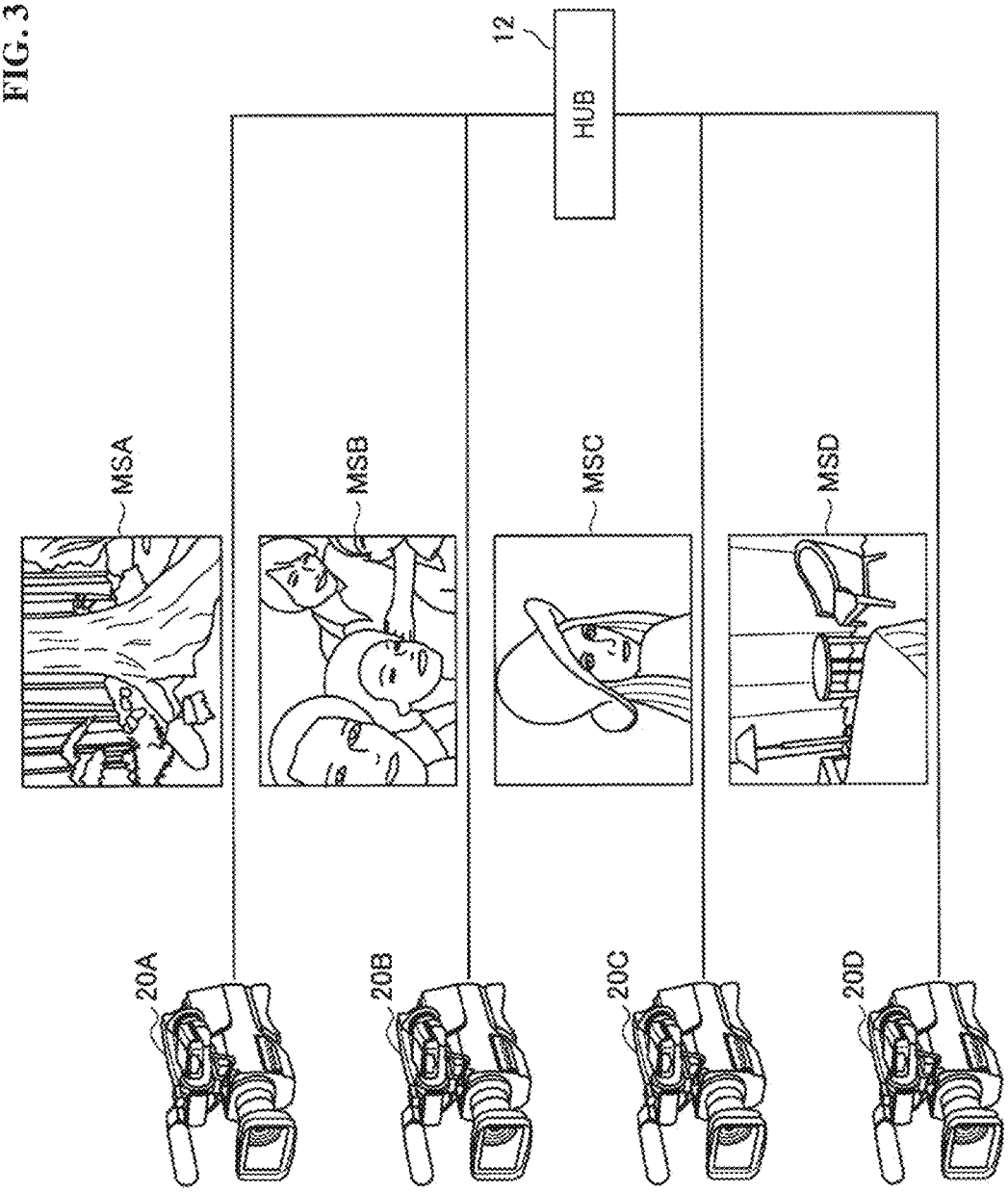
FIG. 3 is an explanatory diagram illustrating transmission of streaming according to a comparative example.

As a method for obtaining the display screen of the display section 42 illustrated in FIG. 2, a method is conceivable in which, as illustrated in FIG. 3, the streaming transmission apparatuses 20A to 20D transmit main streaming MSA to main streaming MSD with high bit rates which corresponds to the main videos MVA to MVD. In the method, the main video MV corresponding to any main streaming MS, and the sub-videos SVA to SVD obtained by resizing the main videos MVA to MVD corresponding to the main streaming MSA to the main streaming MSD are displayed on the display section 42. However, in the method, all the streaming transmission apparatuses 20 transmit the main streaming MS with bit rates, so that the amount of consumed network bands is large. In addition, the streaming reception apparatus 30 side bears a load for resizing the videos.

Figure 4:
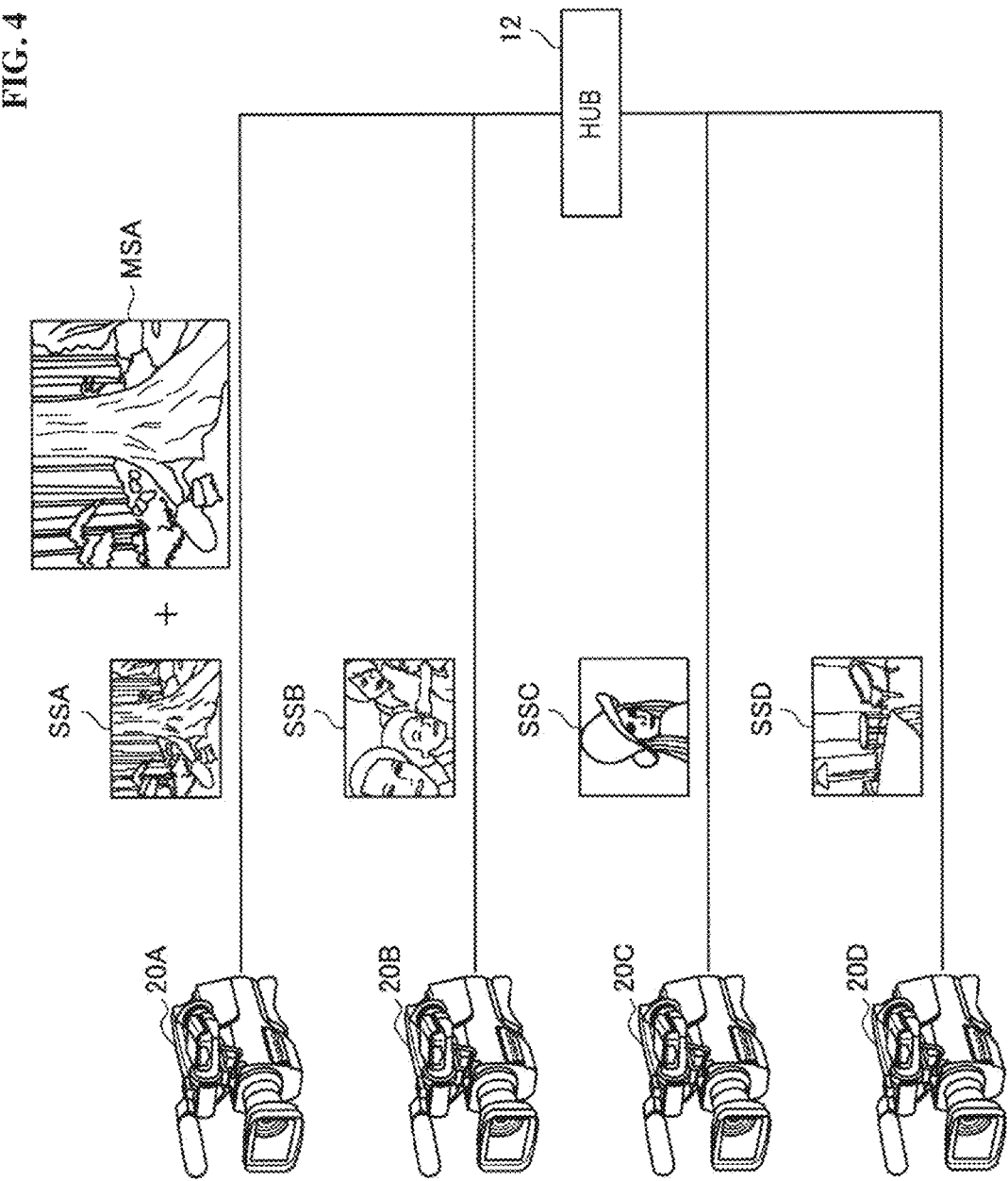
FIG. 4 is an explanatory diagram illustrating transmission of streaming according to an embodiment of the present disclosure.

In contrast, in the display control system according to an embodiment of the present disclosure, as illustrated in FIG. 4, the streaming transmission apparatuses 20A to 20D connected to the streaming reception apparatus 30 transmit sub-streaming SSA to sub-streaming SSD, and one designated streaming transmission apparatus 20 (streaming transmission apparatus 20A in the example illustrated in FIG. 4) transmits main streaming MS. This configuration makes it possible to suppress the amount of consumed network bands. In addition, the streaming reception apparatus 30 can receive the sub-videos SVA to SVD from the sub-streaming SSA to the sub-streaming SSD with no resizing. Note that the bit rate of the main streaming MS transmitted from the streaming transmission apparatuses 20A to 20D may be the same or different. Similarly, the bit rates of the sub-streaming SSA to the sub-streaming SSD transmitted from the streaming transmission apparatuses 20A to 20D may be the same or different. The following describes the configurations of the streaming transmission apparatus 20 and the streaming reception apparatus 30 in such a display control system according to an embodiment of the present disclosure one by one in detail.

2. Configuration of Streaming Transmission Apparatus

Figure 5:
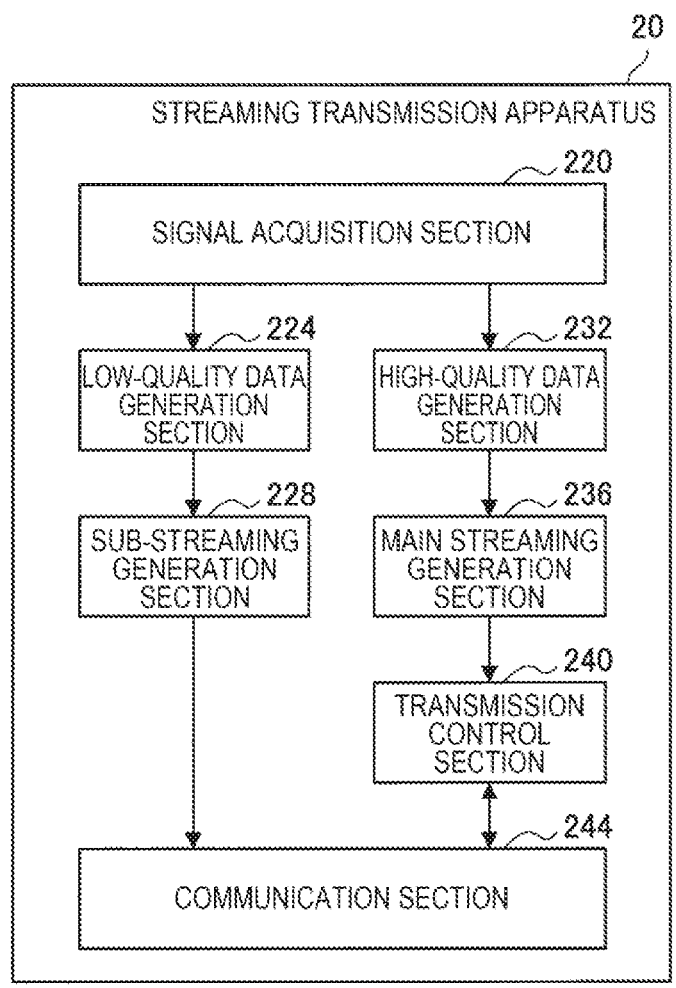
FIG. 5 is an explanatory diagram illustrating a configuration of a streaming transmission apparatus according to an embodiment of the present disclosure.

FIG. 5 is an explanatory diagram illustrating the configuration of the streaming transmission apparatus 20 according to an embodiment of the present disclosure. As illustrated in FIG. 5, the streaming transmission apparatus 20 according to an embodiment of the present disclosure includes a signal acquisition section 220, a low-quality data generation section 224, a sub-streaming generation section 228, a high-quality data generation section 232, a main streaming generation section 236, a transmission control section 240, and a communication section 244.

(Content Acquisition Section)

The signal acquisition section 220 acquires video signals including video data. For example, the video data includes image data, and the image data may be acquired by the signal acquisition section 220 functioning as an imaging section. In addition, the video data may include sound data, and the sound data may be acquired by the signal acquisition section 220 functioning as a sound pickup section.

(Low-Quality Data Generation Section and Sub-Streaming Generation Section)

The low-quality data generation section 224 and the sub-streaming generation section 228 are examples of generation sections that generate the sub-streaming of video data. Specifically, the low-quality data generation section 224 compresses and encodes the video data acquired by the signal acquisition section 220 to generate low-quality video data. The sub-streaming generation section 228 then packetizes the low-quality video data generated by the low-quality data generation section 224, and generates sub-streaming (streaming of low-quality video data) with a low bit rate (first bit rate).

(High-Quality Data Generation Section and Main Streaming Generation Section)

The high-quality data generation section 232 and the main streaming generation section 236 are examples of generation sections that generate the sub-streaming of video data. Specifically, the high-quality data generation section 232 compresses and encodes the video data acquired by the signal acquisition section 220 to generate high-quality video data. The main streaming generation section 236 then packetizes the high-quality video data generated by the high-quality data generation section 232, and generates main streaming (streaming of high-quality video data) with a high bit rate (second bit rate).

(Transmission Control Section)

The transmission control section 240 has a function of controlling a transmission start and a transmission stop of main streaming generated by the main streaming generation section 236. For example, on the basis of the reception of a main streaming transmission start request from the streaming reception apparatus 30, the transmission control section 240 may cause the high-quality data generation section 232 and the main streaming generation section 236 to start to generate main streaming, and provide the generated main streaming to the communication section 244. Note that the high-quality data generation section 232 and the main streaming generation section 236 may generate main streaming before the reception of a main streaming transmission start request.

(Communication Section)

The communication section 244 is an interface between the streaming transmission apparatus 20 and the streaming reception apparatus 30, and has the functions of a transmission section and a reception section. For example, the communication section 244 transmits sub-streaming supplied from the sub-streaming generation section 228 to the streaming reception apparatus 30. In addition, the communication section 244 receives a main streaming transmission start request from the streaming reception apparatus 30, and starts to transmit the main streaming supplied from the transmission control section 240 to the streaming reception apparatus 30 after receiving the main streaming transmission start request.

3. Configuration of Streaming Reception Apparatus

The above describes the configuration of the streaming transmission apparatus 20 with reference to FIG. 5. Next, with reference to FIG. 6, the configuration of the streaming reception apparatus 30 according to an embodiment of the present disclosure will be described.

Figure 6:
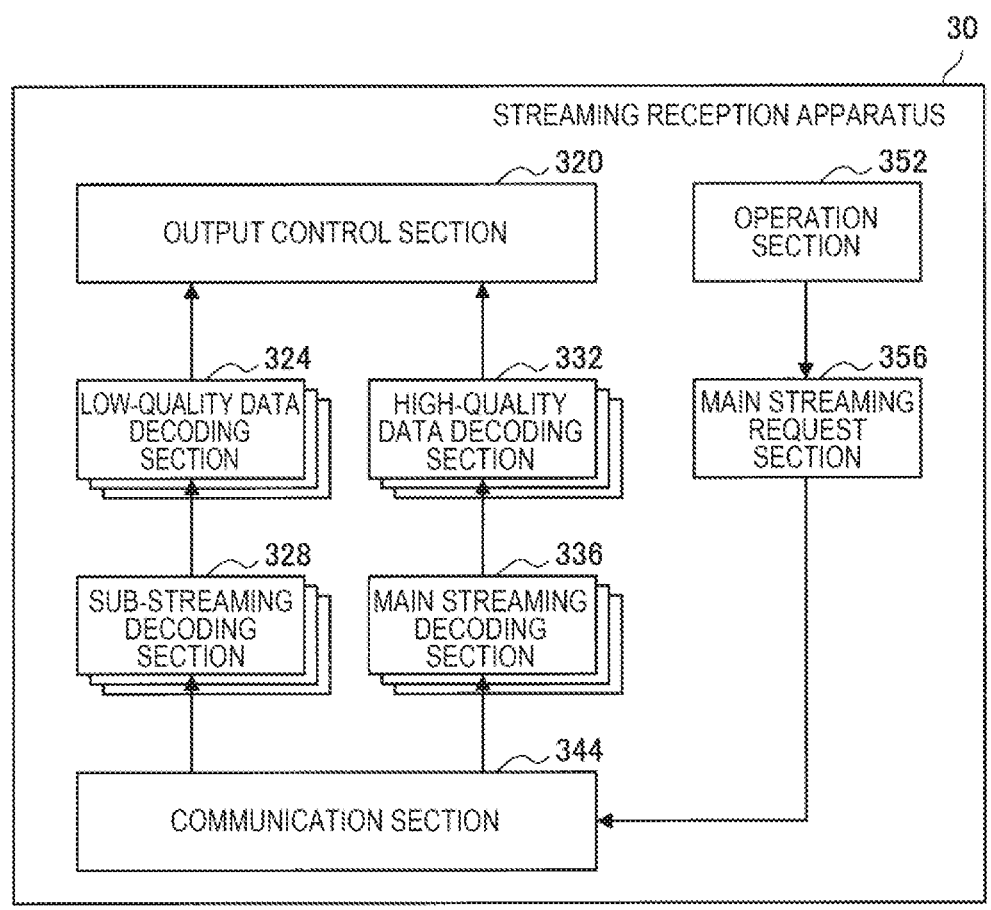
FIG. 6 is an explanatory diagram illustrating a configuration of a streaming reception apparatus according to an embodiment of the present disclosure.

FIG. 6 is an explanatory diagram illustrating the configuration of the streaming reception apparatus 30 according to an embodiment of the present disclosure. As illustrated in FIG. 6, the streaming reception apparatus 30 according to an embodiment of the present disclosure includes an output control section 320, a low-quality data decoding section 324, a sub-streaming decoding section 328, a high-quality data decoding section 332, a main streaming decoding section 336, an operation section 352, and a main streaming request section 356.

(Communication Section)

The communication section 344 is an interface between the plurality of streaming transmission apparatuses 20 and the streaming reception apparatus 30, and has the functions of a transmission section and a reception section. For example, the communication section 344 receives sub-streaming from the plurality of streaming transmission apparatuses 20. In addition, the communication section 344 transmits, on the basis of an instruction from the main streaming request section 356, a main streaming transmission start request to a designated streaming transmission apparatus 20, and then starts to receive main streaming from the streaming transmission apparatus 20.

(Low-Quality Data Decoding Section and Sub-Streaming Decoding Section)

The low-quality data decoding section 324 and the sub-streaming decoding section 328 are examples of decoding sections for obtaining decoded data of low quality from sub-streaming received from the streaming transmission apparatus 20. Specifically, the sub-streaming decoding section 328 extracts low-quality video data from the sub-streaming received from the streaming transmission apparatus 20. The low-quality data decoding section 324 then decodes the low-quality video data extracted by the sub-streaming decoding section 328 to obtain decoded data of low quality. Note that as many pairs of the low-quality data decoding section 324 and the sub-streaming decoding section 328 as the streaming transmission apparatuses 20 connected to the streaming reception apparatus 30 are present.

(High-Quality Data Decoding Section and Main Streaming Decoding Section)

The high-quality data decoding section 332 and the main streaming decoding section 336 are examples of decoding sections for obtaining decoded data of high quality from sub-streaming received from the streaming transmission apparatus 20. Specifically, the main streaming decoding section 336 extracts high-quality video data from the main streaming received from the streaming transmission apparatus 20. The high-quality data decoding section 332 then decodes the high-resolution data extracted by the main streaming decoding section 336 to obtain decoded data of high quality. Note that as many pairs of the high-quality data decoding section 332 and the main streaming decoding section 336 as the streaming transmission apparatuses 20 connected to the streaming reception apparatus 30 are present, or as many pairs of the high-quality data decoding section 332 and the main streaming decoding section 336 as the streaming transmission apparatuses 20 that can concurrently transmit main streaming are present.

(Output Control Unit)

The output control section 320 has the function of a display output section that outputs a video which is displayed on the display apparatus 40 to the display apparatus 40, and the function of a sound output section that outputs a sound which is output from the display apparatus 40 to the display apparatus 40. For example, the output control section 320 generates a sub-video on the basis of decoded data of low quality obtained by the low-quality data decoding section 324, generates a main video on the basis of decoded data of high quality obtained by the high-quality data decoding section 332, and causes the display apparatus 40 to display a display screen including the sub-video and the main video. In the case where the decoded data of low quality or the decoded data of high quality includes a sound, the output control section 320 generates a sound from the decoded data, and causes the display apparatus 40 to output the sound.

(Operation Section)

The operation section 352 is a component operated by a user to input an instruction or information into the streaming reception apparatus 30. For example, the user can perform a main streaming transmission start operation on the operation section 352 to request a certain streaming transmission apparatus 20 to start to transmit main streaming.

(Main Streaming Request Section)

The main streaming request section 356 requests the streaming transmission apparatus 20 designated by a user to start to main streaming on the basis of a main streaming transmission start operation on the operation section 352. Specifically, the main streaming request section 356 supplies the communication section 344 with a main streaming transmission start request (request signal) in which the streaming transmission apparatus 20 is designated, and the communication section 344 transmits the main streaming transmission start request to the designated streaming transmission apparatus 20.

Note that a trigger for the main streaming request section 356 to supply a main streaming transmission start request to the communication section 344 is not limited to an operation made by a user. For example, the main streaming request section 356 may supply the communication section 344 with main streaming transmission start requests in which the different streaming transmission apparatuses 20 that are regularly designated, or supply the communication section 344 with a main streaming transmission start request in which the streaming transmission apparatus 20 corresponding to an analysis result of a sub-video is designated. As the analysis result of a sub-video, a result of object analysis, a result of motion analysis, and the like are included. The result of object analysis may be, for example, person information resulting from face recognition, a person, a substance, or background recognized on the basis of video color information, or a sensing result of sound pressure.

4. Operation Examples

The above describes the configurations of the streaming transmission apparatus 20 and streaming reception apparatus 30 according to an embodiment of the present disclosure. Next, some operation examples of the streaming transmission apparatus 20 and streaming reception apparatus 30 according to an embodiment of the present disclosure will be described one by one in detail.

4-1. First Operation Example (Operation of Streaming Transmission Apparatus)

Figure 7:
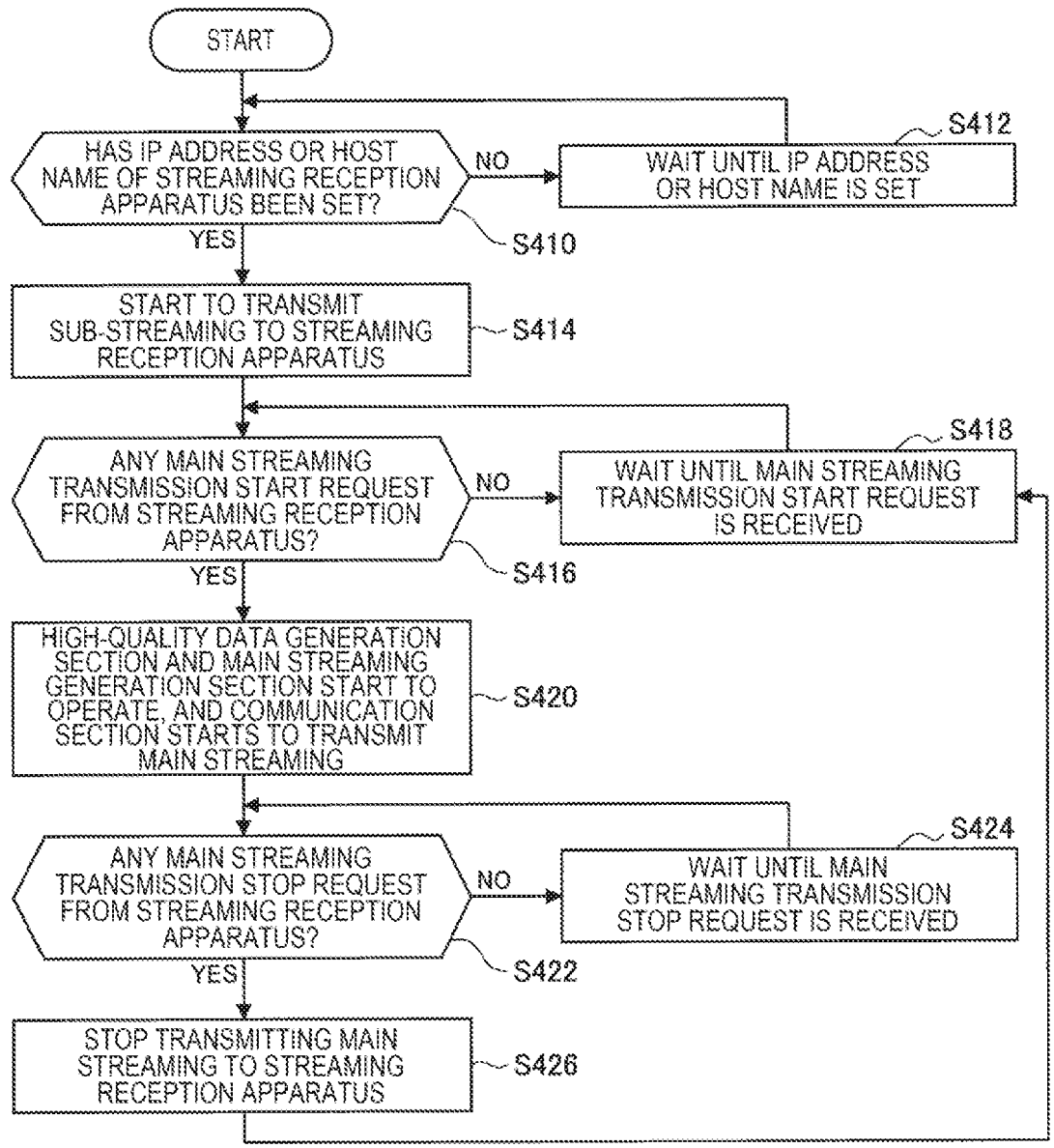
FIG. 7 is a flowchart illustrating a first operation example of the streaming transmission apparatus.

FIG. 7 is a flowchart illustrating a first operation example of the streaming transmission apparatus 20. As illustrated in FIG. 7, in the case where the IP address or host name of the streaming reception apparatus 30 has not yet been set (S410/No), the streaming transmission apparatus 20 waits for the IP address or the host name to be set (S412). After the IP address or the host name is set (S410/Yes), the streaming transmission apparatus 20 then starts to transmit sub-streaming to the streaming reception apparatus 30 (S414).

The streaming transmission apparatus 20 then waits to receive a main streaming transmission start request from the streaming reception apparatus 30 (S416/No, and S418). Once the streaming transmission apparatus 20 receives a main streaming transmission start request from the streaming reception apparatus 30 (S416/Yes), the high-quality data generation section 232 and the main streaming generation section 236 start to operate, and the communication section 244 starts to transmit main streaming (S420).

Afterward, the streaming transmission apparatus 20 then waits to receive a main streaming transmission stop request from the streaming reception apparatus 30 (S422/No, and S424). Once the streaming transmission apparatus 20 receives a main streaming transmission stop request from the streaming reception apparatus 30 (S422/Yes), the high-quality data generation section 232 and the main streaming generation section 236 stop the operation, and the communication section 244 stops transmitting the main streaming to the streaming reception apparatus 30 (S426). The streaming transmission apparatus 20 then repeats the processing from S418.

(Operation of Streaming Reception Apparatus)

Figure 8:
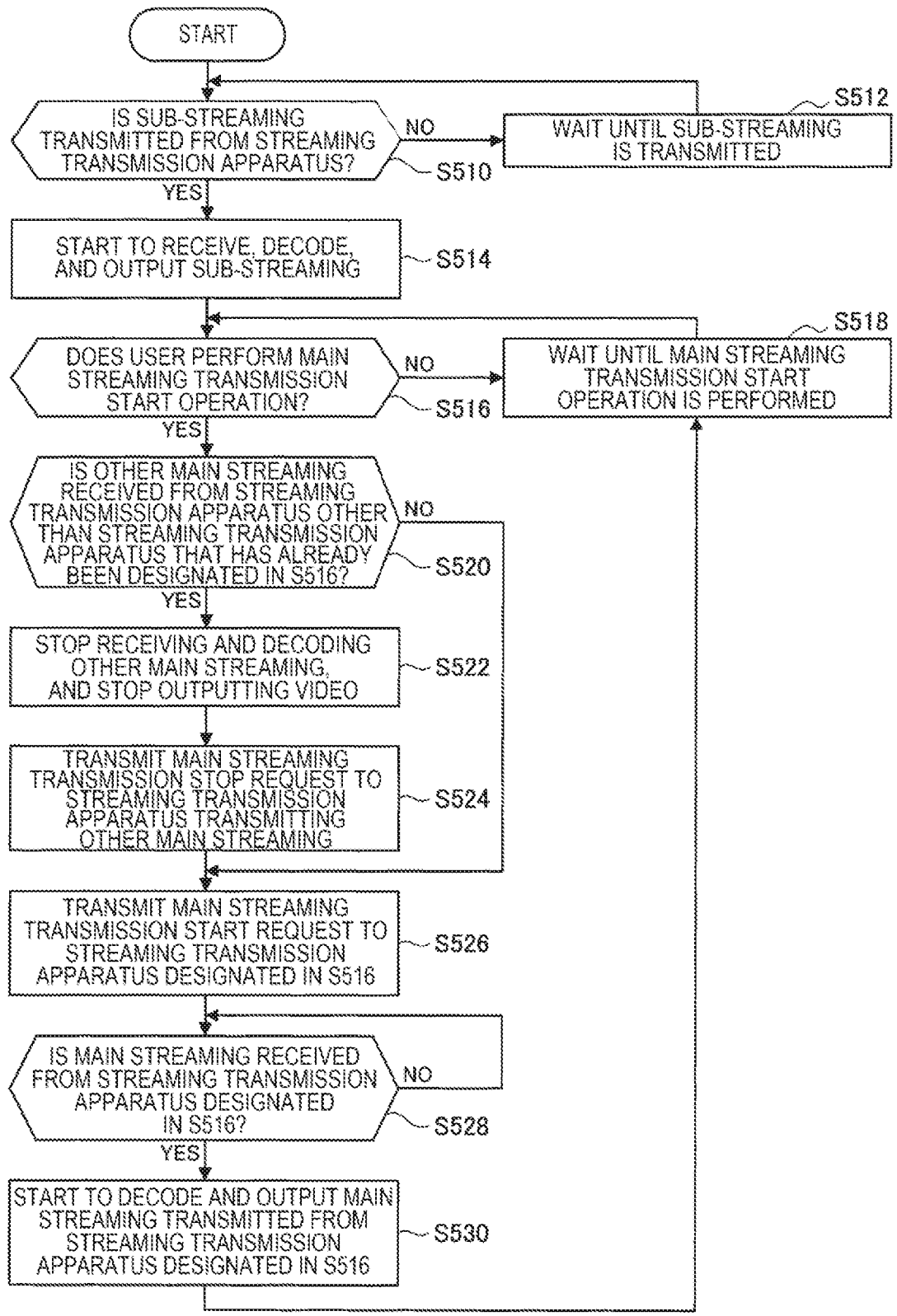
FIG. 8 is a flowchart illustrating a first operation example of the streaming reception apparatus.

FIG. 8 is a flowchart illustrating a first operation example of the streaming reception apparatus 30. As illustrated in FIG. 8, the streaming reception apparatus 30 waits for the streaming transmission apparatus 20 to transmit sub-streaming (S510/No, and S512). Once the streaming transmission apparatus 20 transmits sub-streaming, the communication section 344 then receives the sub-streaming, the sub-streaming decoding section 328 and the low-quality data decoding section 324 start to operate, and the output control section 320 starts to output a sub-video (S514).

Afterward, the streaming reception apparatus 30 waits for a user to perform a main streaming transmission start operation (S516/No, and S518). In the case where the user then performs a main streaming transmission start operation (S516/Yes), the streaming reception apparatus 30 determines whether other main streaming is received from the streaming transmission apparatus 20 other than the streaming transmission apparatus 20 designated according to the main streaming transmission start operation (S520). In the case where other main streaming is not received (S520/No), the streaming reception apparatus 30 proceeds to the processing in S526.

In contrast, in the case where the streaming reception apparatus 30 receives other main streaming, the communication section 344 stops the reception of the other main streaming, the main streaming decoding section 336 and the high-quality data decoding section 332 stop the operations for the other main streaming, and the output control section 320 stops outputting the main video corresponding to the other main streaming (S522). Further, the communication section 344 transmits a main streaming transmission stop request to the streaming transmission apparatus 20 transmitting the other main streaming (S524).

Afterward, the communication section 344 transmits a main streaming transmission start request to the streaming transmission apparatus 20 designated in S516 (S526). Once the communication section 344 receives main streaming from the streaming transmission apparatus 20 designated in S516 (S528/Yes), the main streaming decoding section 336 and the high-quality data decoding section 332 start the operations for the main streaming, and the output control section 320 starts to output the main video corresponding to the main streaming (S530). The streaming reception apparatus 30 then repeats the processing from S518.

Figure 9:
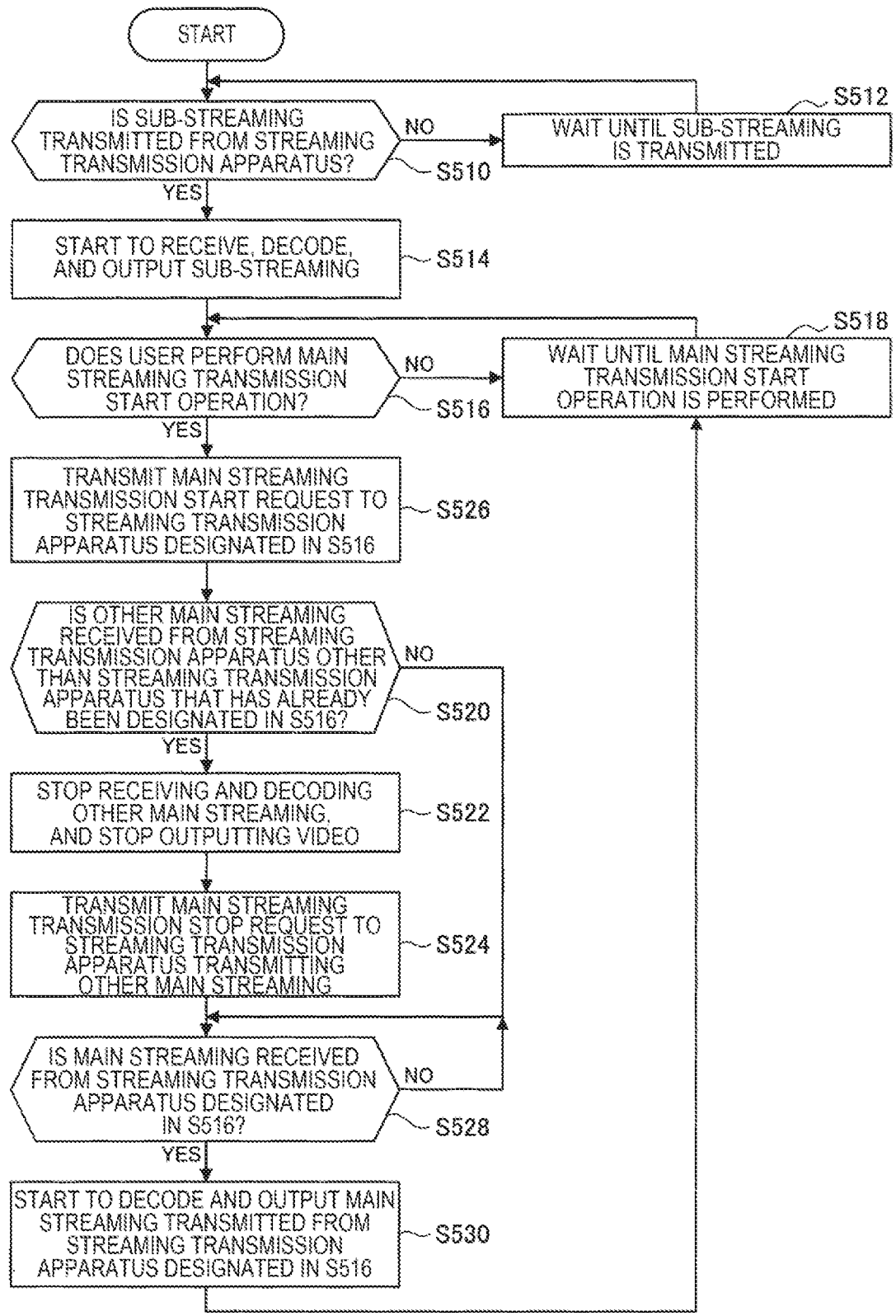
FIG. 9 is a flowchart illustrating an operation of a streaming reception apparatus according to a modified example.

Note that an example has been described in which the streaming reception apparatus 30 transmits, in S524, a main streaming transmission stop request for other main streaming in FIG. 8, and then transmits a main streaming transmission start request to the streaming transmission apparatus 20 newly designated in S526, but the timing at which a main streaming transmission start request is transmitted is not limited to the example illustrated in FIG. 8. With reference to FIG. 9, the following describes a modified example of the timing at which a main streaming transmission start request is transmitted.

FIG. 9 is a flowchart illustrating the operation of the streaming reception apparatus 30 according to a modified example. In the modified example, as illustrated in FIG. 9, before the determination regarding whether or not other main streaming is received (S520) to the transmission of a main streaming transmission stop request for the other main streaming (S524), a main streaming transmission start request is transmitted to the newly designated streaming transmission apparatus 20 (S526).

According to such a modified example, it is possible to reduce the amount of delay caused from a main streaming transmission start operation of a user to designate the new streaming transmission apparatus 20 to a displayed main image based on main streaming transmitted from the new streaming transmission apparatus 20.

(System Operation)

Figure 10:
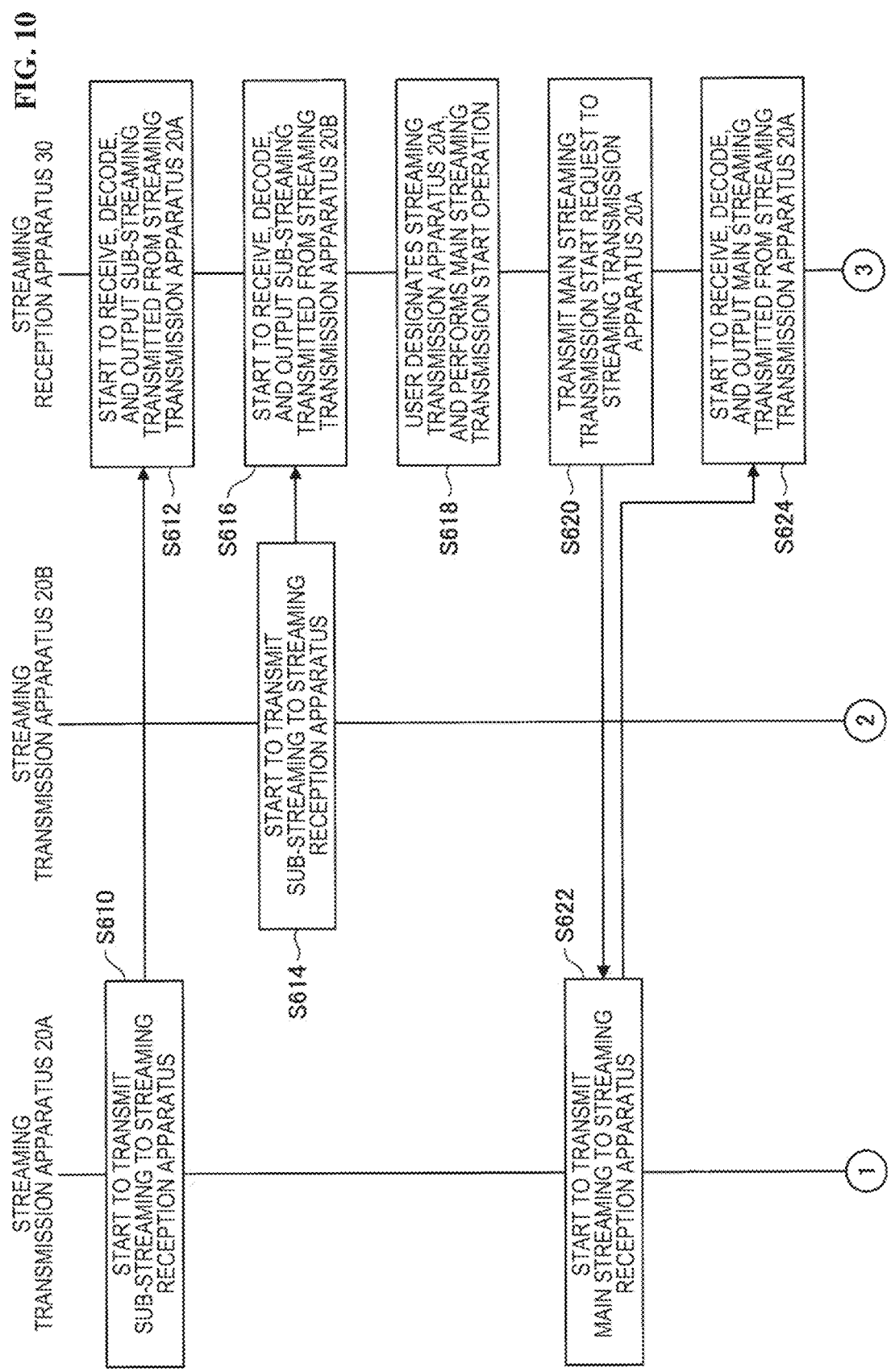
FIG. 10 is an explanatory diagram illustrating a first operation example of a display control system.
Figure 11:
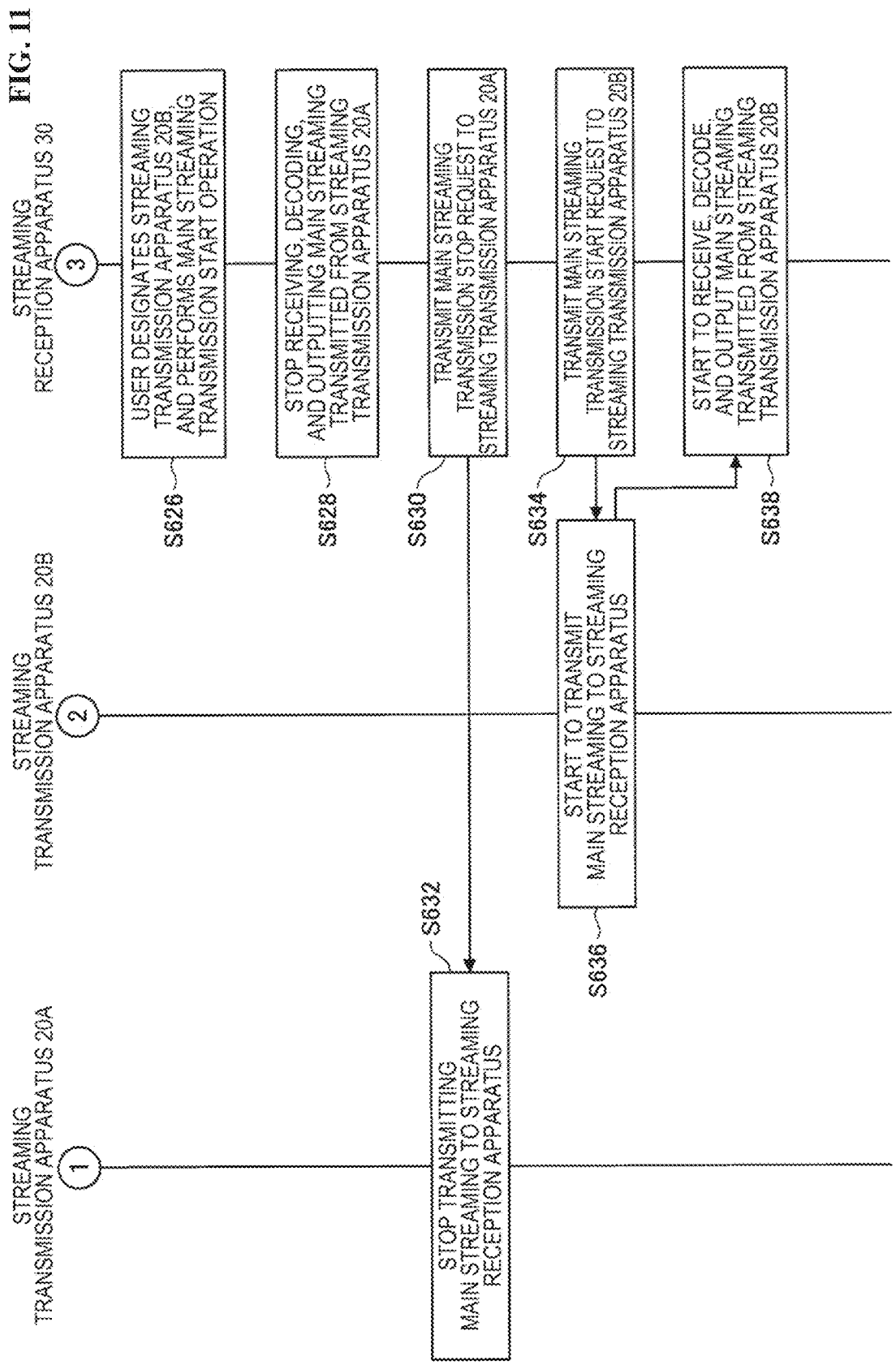
FIG. 11 is an explanatory diagram illustrating the first operation example of the display control system.

Next, with reference to FIGS. 10 and 11, the overall operation of the display control system will be summarized.

FIGS. 10 and 11 are explanatory diagrams each illustrating a first operation example of the display control system. As illustrated in FIG. 10, once the streaming transmission apparatus 20A starts to transmit sub-streaming to the streaming reception apparatus 30 (S610), the streaming reception apparatus 30 starts to receive and decode the sub-streaming transmitted from the streaming transmission apparatus 20A, and starts to output a sub-video (S612). Similarly, once the streaming transmission apparatus 20B starts to transmit sub-streaming to the streaming reception apparatus 30 (S614), the streaming reception apparatus 30 starts to receive and decode the sub-streaming transmitted from the streaming transmission apparatus 20B, and starts to output a sub-video (S616).

Afterward, once a user designates the streaming transmission apparatus 20A to perform a main streaming transmission start operation (S618), the streaming reception apparatus 30 transmits a main streaming transmission start request to the streaming transmission apparatus 20A (S620). The streaming transmission apparatus 20A starts to transmit main streaming to the streaming reception apparatus 30 on the basis of the reception of the main streaming transmission start request (S622). The streaming reception apparatus 30 starts to receive and decode the main streaming transmitted from the streaming transmission apparatus 20A, and starts to output a main video (S624).

Then, once a user designates the streaming transmission apparatus 20B to perform a main streaming transmission start operation (S626), the streaming reception apparatus 30 stops receiving and decoding the main streaming transmitted from the streaming transmission apparatus 20A, and stops outputting the main video (S628). Further, the streaming reception apparatus 30 transmits a transmission stop request for main streaming to the streaming transmission apparatus 20A (S630), and the streaming transmission apparatus 20A stops transmitting the main streaming to the streaming reception apparatus 30 (S632).

Afterward, the streaming reception apparatus 30 transmits a main streaming transmission start request to the streaming transmission apparatus 20B (S634). The streaming transmission apparatus 20B starts to transmit main streaming to the streaming reception apparatus 30 on the basis of the reception of the main streaming transmission start request (S636). The streaming reception apparatus 30 starts to receive and decode the main streaming transmitted from the streaming transmission apparatus 20B, and starts to output a main video (S638).

Effect

According to the first operation example as described above, each streaming transmission apparatus 20 transmits sub-streaming, and the streaming transmission apparatus 20 that receives a main streaming transmission start request further transmits main streaming. This configuration makes it possible to suppress the amount of consumed network bands as compared with the case where all the streaming transmission apparatuses 20 transmit main streaming. In addition, the streaming reception apparatus 30 can obtain a sub-video from sub-streaming with no resizing, so that it is also possible to reduce the processing load on the streaming reception apparatus 30.

In addition, according to the first operation example, the streaming transmission apparatus 20 that receives a main streaming transmission start request concurrently transmit both main streaming and sub-streaming. Therefore, the streaming reception apparatus 30 can display a main video on the basis of the main streaming transmitted from the streaming transmission apparatus 20 that receives a main streaming transmission start request, and display a sub-video on the basis of the sub-streaming in parallel. That is, it is possible to concurrently display the main video and sub-video corresponding to the same video data. The following describes the meaning that the main video and sub-video corresponding to the same video data are concurrently displayed.

A comparative example is considered in which a first display apparatus for displaying a main video and a second display apparatus for displaying plurality of sub-videos are present as different entities, and the sub-videos corresponding to a main video displayed on the first display apparatus are not displayed on the second display apparatus. In this comparative example, it is difficult for a user watching the second display apparatus to obtain information regarding the main video displayed on the first display apparatus.

Figure 12:
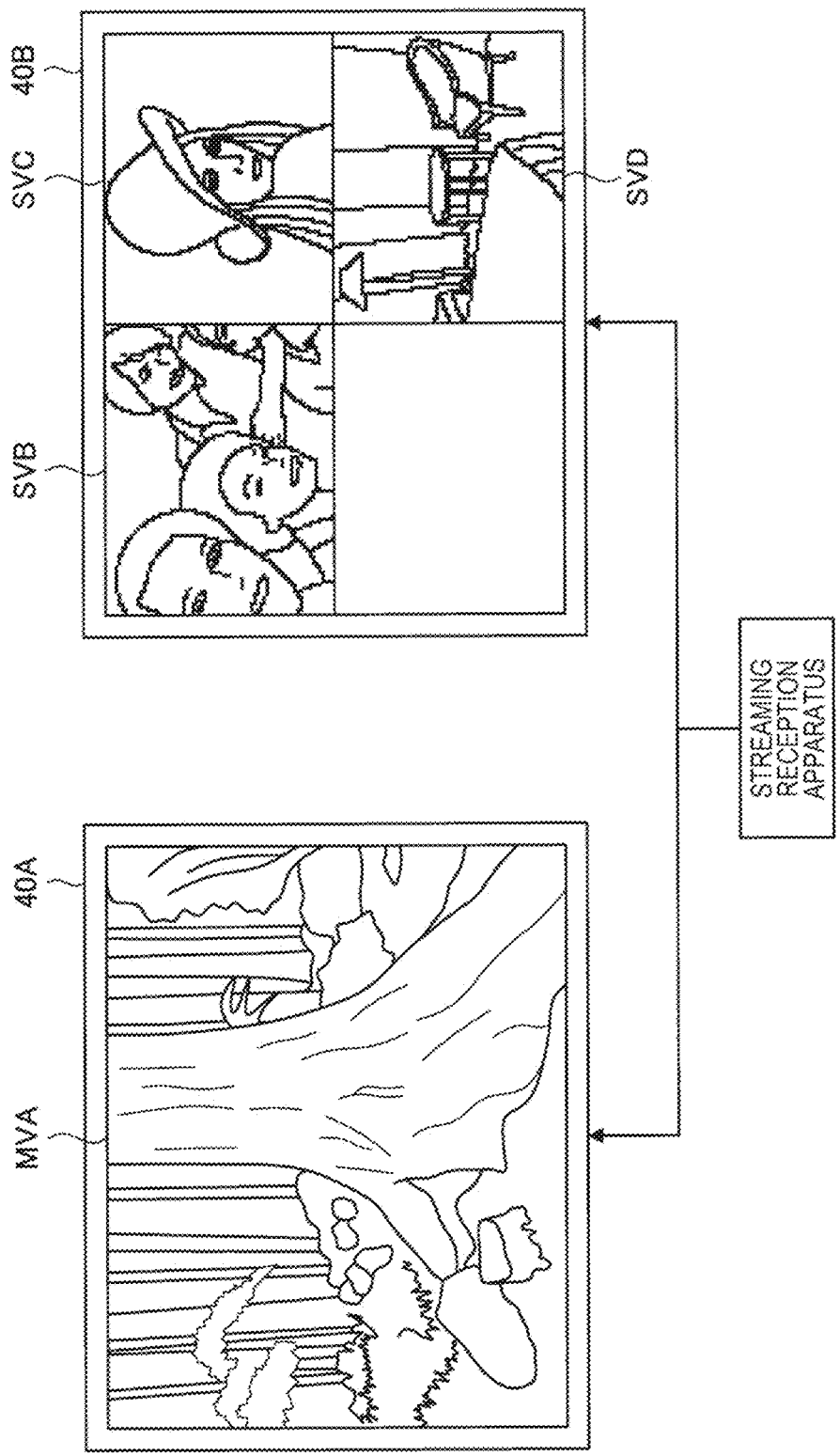
FIG. 12 is an explanatory diagram illustrating a display example of a video according to a comparative example.

For example, as illustrated in FIG. 12, in the case where a display apparatus 40A that displays a main video MVA, and a display apparatus 40B that displays sub-videos SVB to SVD are present, it is difficult for a user watching the display apparatus 40B to obtain information regarding the main video MVA. In contrast, according to the first operation example, the display apparatus 40B displays the sub-video SVA corresponding to the main video MVA, so that it is also possible for the user watching the display apparatus 40B to obtain the information regarding the main video MVA displayed on the display apparatus 40A.

Figure 13:
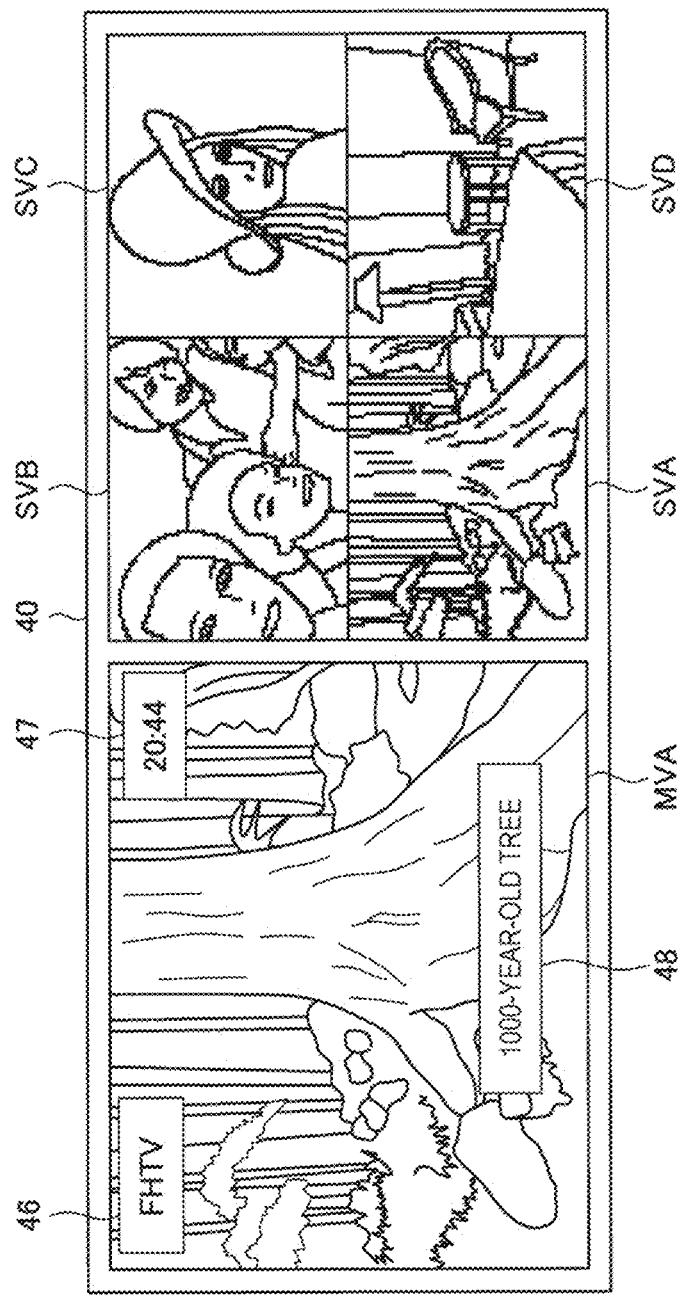
FIG. 13 is an explanatory diagram illustrating a display example of a video according to an embodiment of the present disclosure.

In addition, even in the case where the same display apparatus 40 displays a main video and a plurality of sub-videos, it is of use to concurrently display a main video based on main streaming and sub-videos based on sub-streaming which are transmitted from the same streaming transmission apparatus 20. For example, in the broadcasting system, as illustrated in FIG. 13, as the main video MVA, a live-edited video is sometimes displayed on which a logotype 46, displayed time 47, a telop 48, and the like are superimposed. Besides, in the case where video data pertains to sports, a scoreboard can be superimposed. Even in such a case, displaying the original video as the sub-video SVA allows a user to check the state of the main video MVA that has not yet been edited.

(Supplemental Information)

Here, supplemental information will be given regarding how to further suppress network bands to be consumed.

Figure 14:
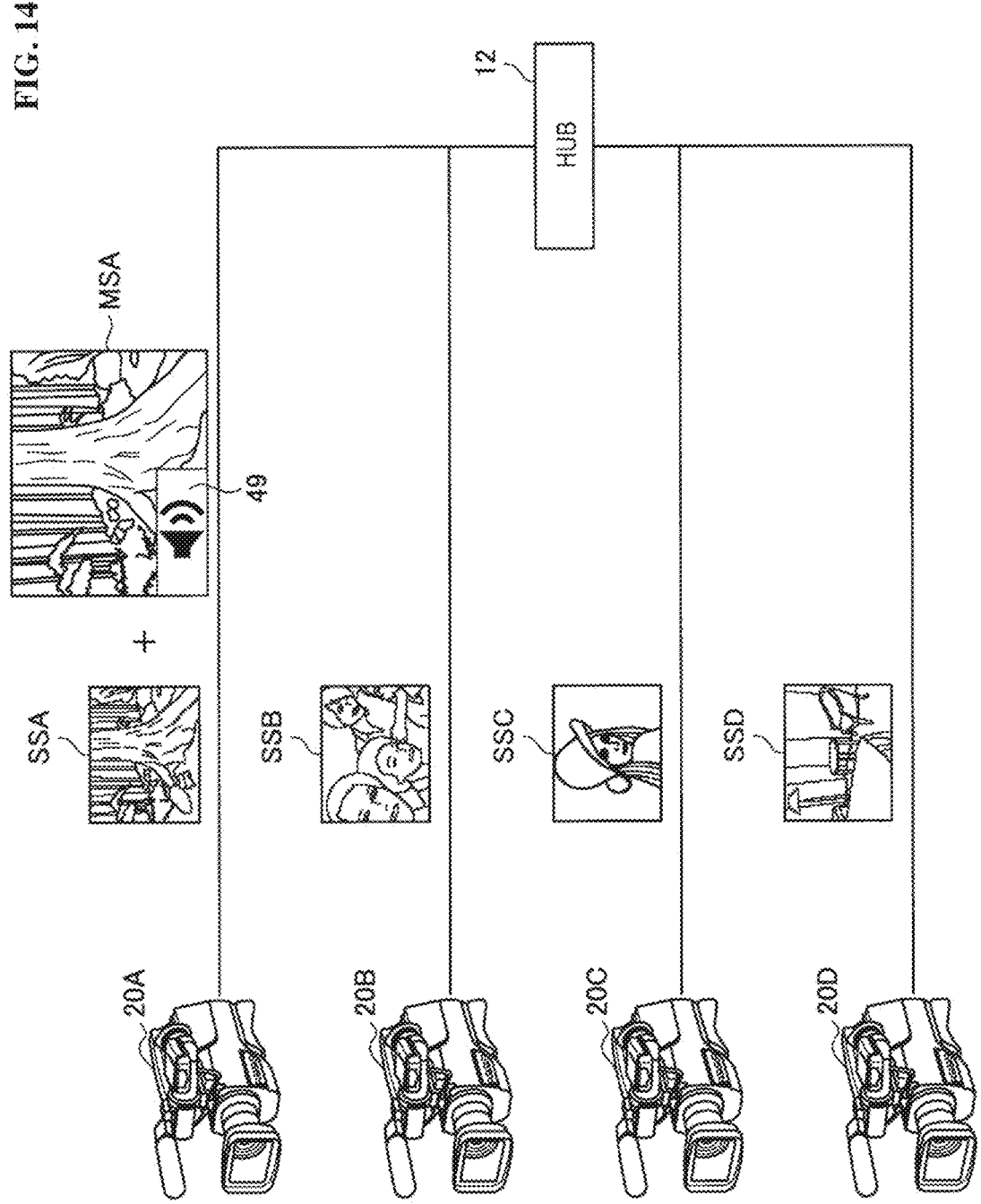
FIG. 14 is an explanatory diagram illustrating transmission of streaming according to the first operation example.

For example, while the main streaming transmitted by the streaming transmission apparatus 20 includes sound data, the sub-streaming transmitted by the streaming transmission apparatus 20 does not have to include sound data. For example, as illustrated in FIG. 14, while the main streaming MSA includes sound data 49, the sub-streaming SSA to sub-streaming SSD do not have to include the sound data 49. This configuration makes it possible to suppress network bands to be consumed for the communication of the sub-streaming SSA to the sub-streaming SSD. In addition, it is also possible to reduce the load on the streaming transmission apparatus 20 and the streaming reception apparatus 30 to process sound data.

Alternatively, the proportion of the information amount of color differences to the information amount of luminance in the sub-streaming transmitted by the streaming transmission apparatus 20 may be lower than the proportion of the information amount of color differences to the information amount of luminance in the main streaming. For example, the sub-streaming does not have to include information of color differences. In this case, it is possible to suppress the amount of consumed network bands for transmitting sub-streaming. The streaming reception apparatus 30 can skip the processing regarding color differences. In addition, the streaming transmission apparatus 20 may transmit sub-streaming in which information of color differences is decimated. For example, in the case where the proportion of luminance (Y) and color differences (U and V) before decimation is 4:4:4, the proportion of luminance (Y) and color differences (U and V) after decimation may be 4:2:2 or 4:2:0. The decimation can also suppress the amount of consumed network bands for transmitting sub-streaming.

4-2. Second Operation Example

The above describes the first operation example. Next, a second operation example will be described. The second operation example is different from the first operation example chiefly in the operation of the streaming transmission apparatus 20. Accordingly, the following describes the operation of the streaming transmission apparatus 20.

Figure 15:
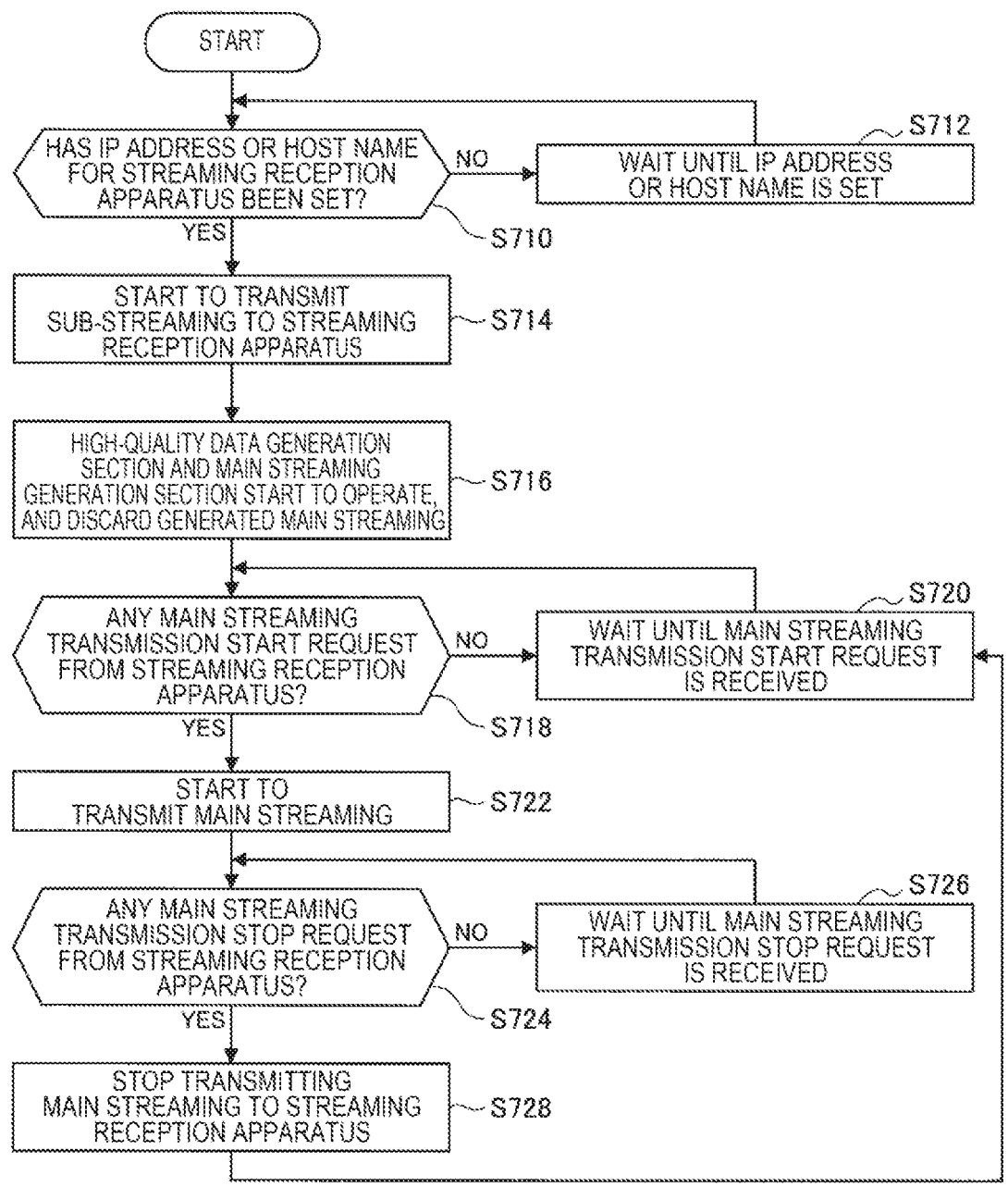
FIG. 15 is a flowchart illustrating a second operation example of the streaming transmission apparatus.

FIG. 15 is a flowchart illustrating a second operation example of the streaming transmission apparatus 20. As illustrated in FIG. 15, in the case where the IP address or host name of the streaming reception apparatus 30 has not yet been set (S710/No), the streaming transmission apparatus 20 waits for the IP address or the host name to be set (S712). After the IP address or the host name is set (S710/Yes), the streaming transmission apparatus 20 then starts to transmit sub-streaming to the streaming reception apparatus 30 (S714).

Next, the high-quality data generation section 232 and the main streaming generation section 236 start the operations and the main streaming generation section 236 starts to output main streaming, but the transmission control section 240 discards the main streaming (S716).

The streaming transmission apparatus 20 then waits to receive a main streaming transmission start request from the streaming reception apparatus 30 (S718/No, and S720). Once a main streaming transmission start request is received from the streaming reception apparatus 30 (S718/Yes), the transmission control section 240 starts to supply main streaming to the communication section 244, and the communication section 244 starts to transmit the main streaming (S722).

Afterward, the streaming transmission apparatus 20 waits to receive a main streaming transmission stop request from the streaming reception apparatus 30 (S724/No, and S726). Once the streaming transmission apparatus 20 receives a main streaming transmission stop request from the streaming reception apparatus 30 (S724/Yes), the transmission control section 240 stops supplying the communication section 244 with the main streaming, and the communication section 244 stops supplying the streaming reception apparatus 30 with the main streaming (S728). The streaming transmission apparatus 20 then repeats the processing from S720.

As described above, in the streaming transmission apparatus 20 according to the second operation example, the high-quality data generation section 232 and the main streaming generation section 236 start the operations before a main streaming transmission start request is received. Therefore, it is possible to suppress delay caused from the reception of a main streaming transmission start request to a start of the transmission of main streaming.

Note that the above describes an example in which, before a main streaming transmission start request is received, the high-quality video data generation section 232 and the main streaming generation section 236 start the operations, but the high-quality data generation section 232 alone may start the operation among the high-quality data generation section 232 and the main streaming generation section 236. This configuration also makes it possible to suppress not a little delay. In addition, it is possible to reduce the resources of the main streaming generation section 236 which are consumed for generating main streaming that is not actually transmitted.

In addition, in the case where emphasis is placed on the suppression of delay (switching delay) caused by switching main videos, it is also of use for the streaming transmission apparatus 20 to continue transmitting both sub-streaming and main streaming. In this case, the streaming reception apparatus 30 may keep the main streaming decoding section 336 and the high-quality data decoding section 332 in operation, and acquire or discard decoded data of high quality which is acquired by the high-quality data decoding section 332. This configuration makes it possible to drastically suppress delay caused by switching main streaming.

4-3. Third Operation Example

The above describes the second operation example. Next, a third operation example will be described. The third operation example uses a NEXT function of designating a main video that is displayed next, and suppresses the switching delay of the main videos. First, with reference to FIG. 16, the NEXT function will be described.

The streaming transmission apparatus 20 of the transmission source of the main streaming corresponding to a displayed main video is referred to as PGM in some cases. In contrast, the streaming transmission apparatus 20 corresponding to a main video that is displayed next can be referred to as NEXT. In example illustrated in FIG. 16, the main video MVA is displayed, and the streaming transmission apparatus 20A of the transmission source of the main streaming MSA corresponding to the main video MVA is designated as PGM. In addition, in FIG. 16, the sub-video SVB has NEXT, and the streaming transmission apparatus 20B of the transmission source of the sub-streaming SSB corresponding to the sub-video SVB is designated as NEXT.

A user can designate NEXT by operating the operation section 352. For example, the user may designate NEXT by selecting any of a plurality of displayed sub-videos. The user designates a certain streaming transmission apparatus 20 as NEXT, and then designates the streaming transmission apparatus 20 as PGM to start to display a main video based on main streaming transmitted from the streaming transmission apparatus 20.

In the third operation example, the above-described NEXT function is used to suppress the switching delay of main videos. Specifically, when a certain streaming transmission apparatus 20 is designated as NEXT, the streaming reception apparatus 30 transmits a main streaming transmission start request to the streaming transmission apparatus 20.

Figure 16:
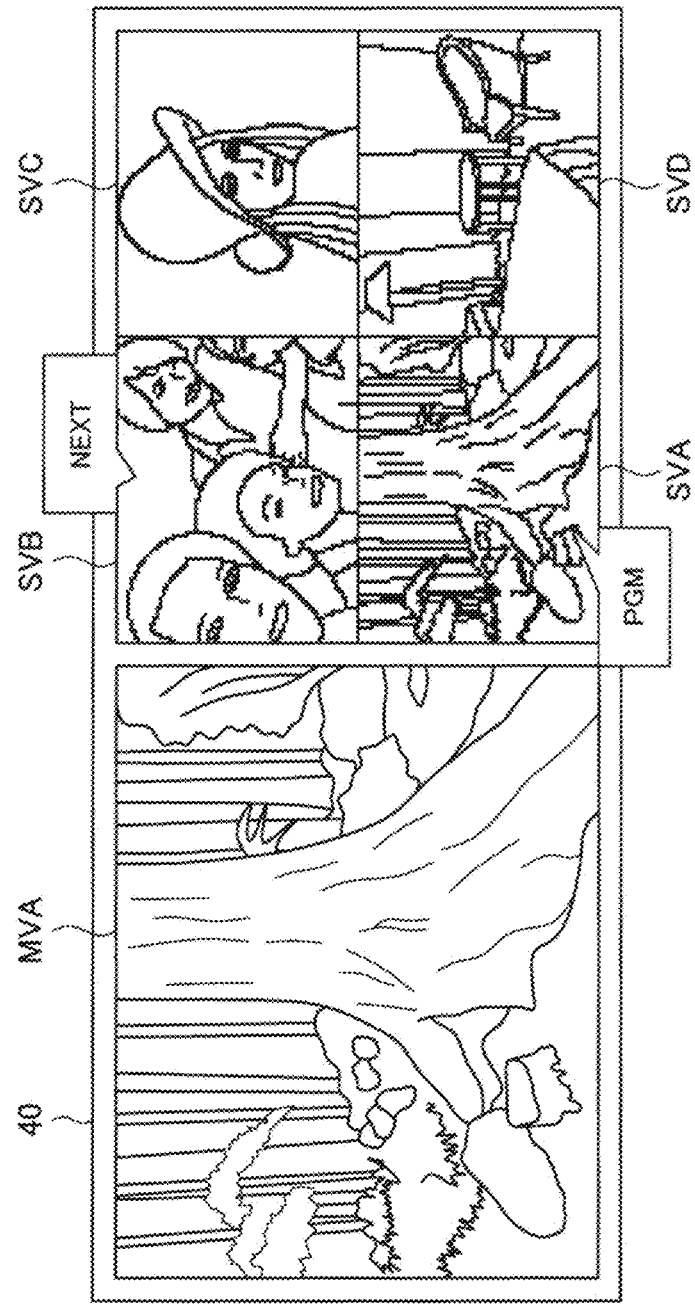
FIG. 16 is an explanatory diagram illustrating a NEXT function.
Figure 17:
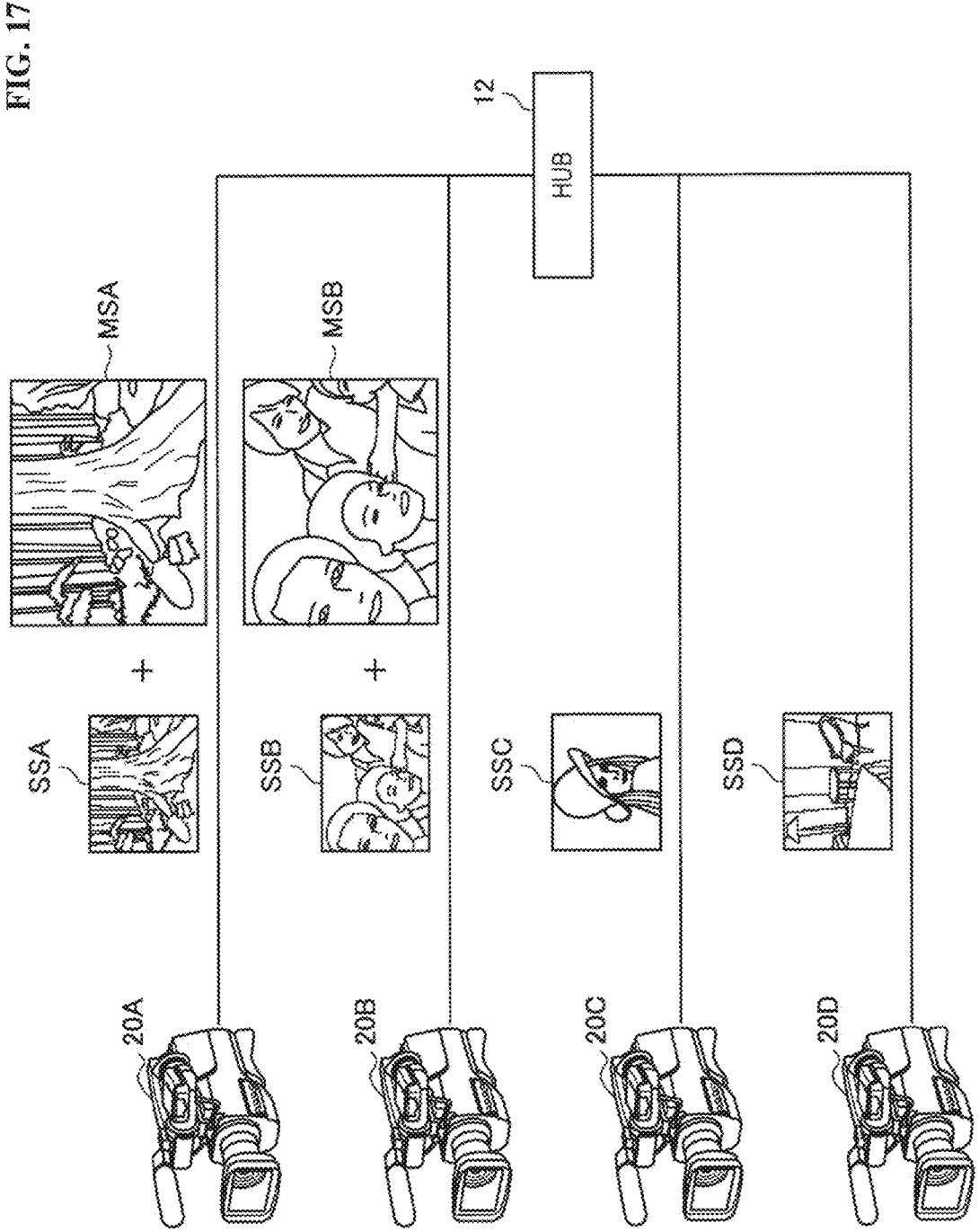
FIG. 17 is an explanatory diagram illustrating transmission of streaming according to a third operation example.

For example, as illustrated in FIG. 16, in the case where the streaming transmission apparatus 20A is designated as PGM and the streaming transmission apparatus 20B is designated as NEXT, the streaming reception apparatus 30 transmits a main streaming transmission start request to the streaming transmission apparatus 20B as a designating signal that designates the next display. As a result, as illustrated in FIG. 17, the streaming transmission apparatus 20A transmits the main streaming MSA, and the streaming transmission apparatus 20B transmits the main streaming MSB. The main streaming decoding section 336 and the high-quality data decoding section 332 of the streaming reception apparatus 30 execute the processing for the main streaming MSB in the background. Then, after the streaming transmission apparatus 20B is designated as PGM, the output control section 320 causes the display apparatus 40 to start to display the main video MVB based on the main streaming MSB. This configuration makes it possible to suppress switching delay caused from the streaming transmission apparatus 20B being designated as PGM to the main video MVB based on the main streaming MSB being displayed.

Figure 18:
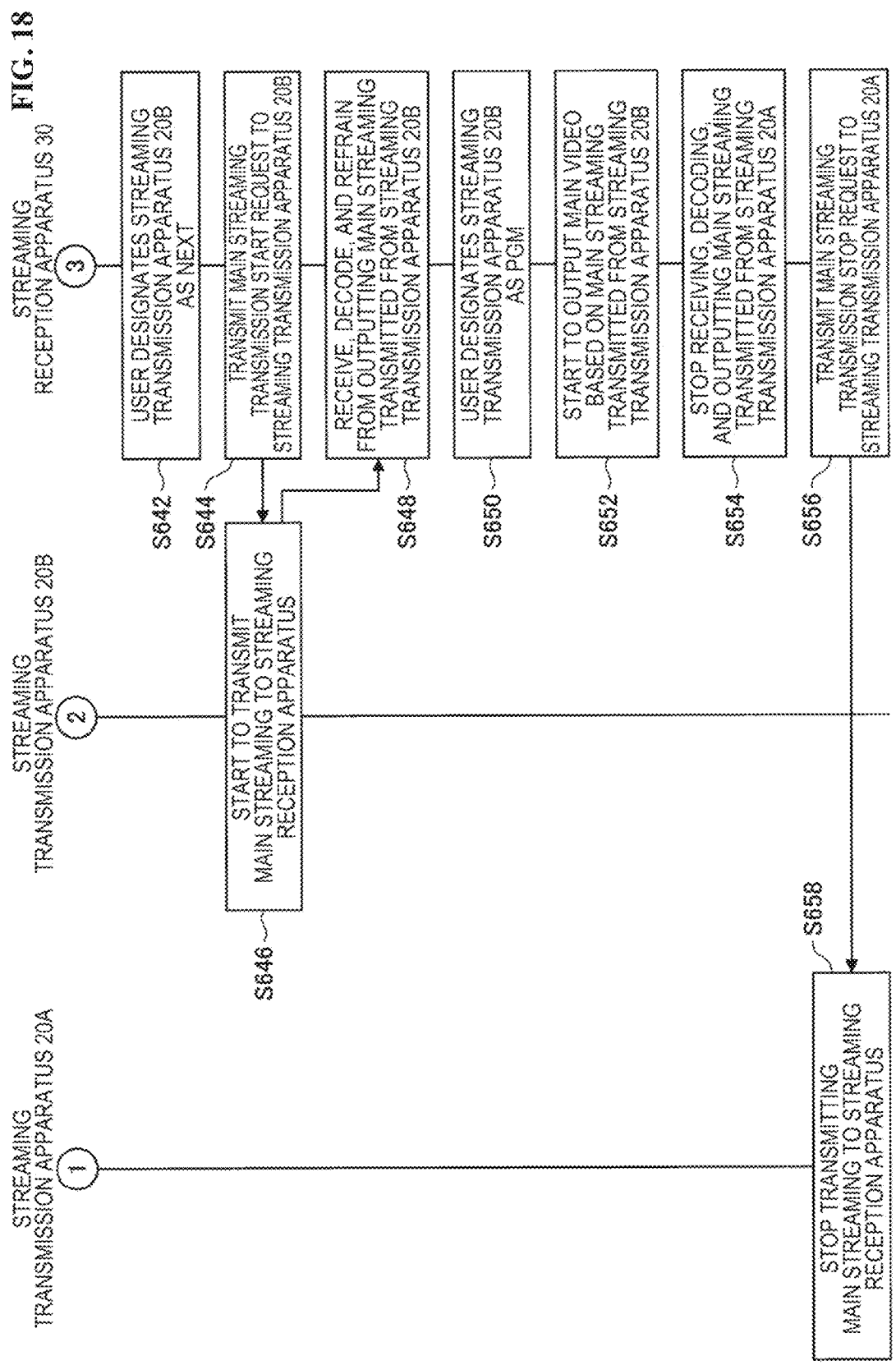
FIG. 18 is an explanatory diagram illustrating the third operation example of the display control system.

With reference to FIG. 18, the following summarizes the above-described third operation example.

FIG. 18 is an explanatory diagram illustrating the third operation example of the display control system. FIG. 18 illustrates processing following the processing illustrated in FIG. 13. That is, FIG. 18 illustrates processing performed after the streaming reception apparatus 30 outputs a main video based on main streaming transmitted from the streaming transmission apparatus 20A.

Once a user designates the streaming transmission apparatus 20B as NEXT (S642), the streaming reception apparatus 30 transmits a main streaming transmission start request to the streaming transmission apparatus 20B (S644). The streaming transmission apparatus 20B starts to transmit main streaming to the streaming reception apparatus 30 on the basis of the reception of the main streaming transmission start request (S646). The streaming reception apparatus 30 starts to receive and decode the main streaming transmitted from the streaming transmission apparatus 20B, but does not output the main video at this time (S648).

Once the user designates the streaming transmission apparatus 20B as PGM afterward according a predetermined operation on a GUI, an operation key, or the like (S650), the streaming reception apparatus 30 starts to output a main video based on the main streaming transmitted from the streaming transmission apparatus 20B (S652). Next, the streaming reception apparatus 30 stops receiving and decoding the main streaming transmitted from the streaming transmission apparatus 20A, and stops outputting the main video (S654). Then, the streaming reception apparatus 30 transmits a transmission stop request for main streaming to the streaming transmission apparatus 20A (S656), and the streaming transmission apparatus 20A stops transmitting the main streaming to the streaming reception apparatus 30 (S658). Note that PGM is not designated on the basis of an operation performed by the user, but may be designated on the basis of a predetermined elapsed time since NEXT is designated, or the fact that a sensor input or the like satisfies a condition set in advance.

According to the third operation example as described above, before, in S650, the streaming transmission apparatus 20B is designated as PGM, the main streaming transmitted from the streaming transmission apparatus 20B is received and decoded. Therefore, after, in S650, the streaming transmission apparatus 20B is designated as PGM, the main video can be switched to a main video based on the main streaming transmitted from the streaming transmission apparatus 20B with less delay.

5. Hardware Configuration

The above describes an embodiment of the present disclosure. Information processing such as the above-described communication control and output control is performed by software cooperating with the hardware of the streaming reception apparatus 30 which will be described below.

Figure 19:
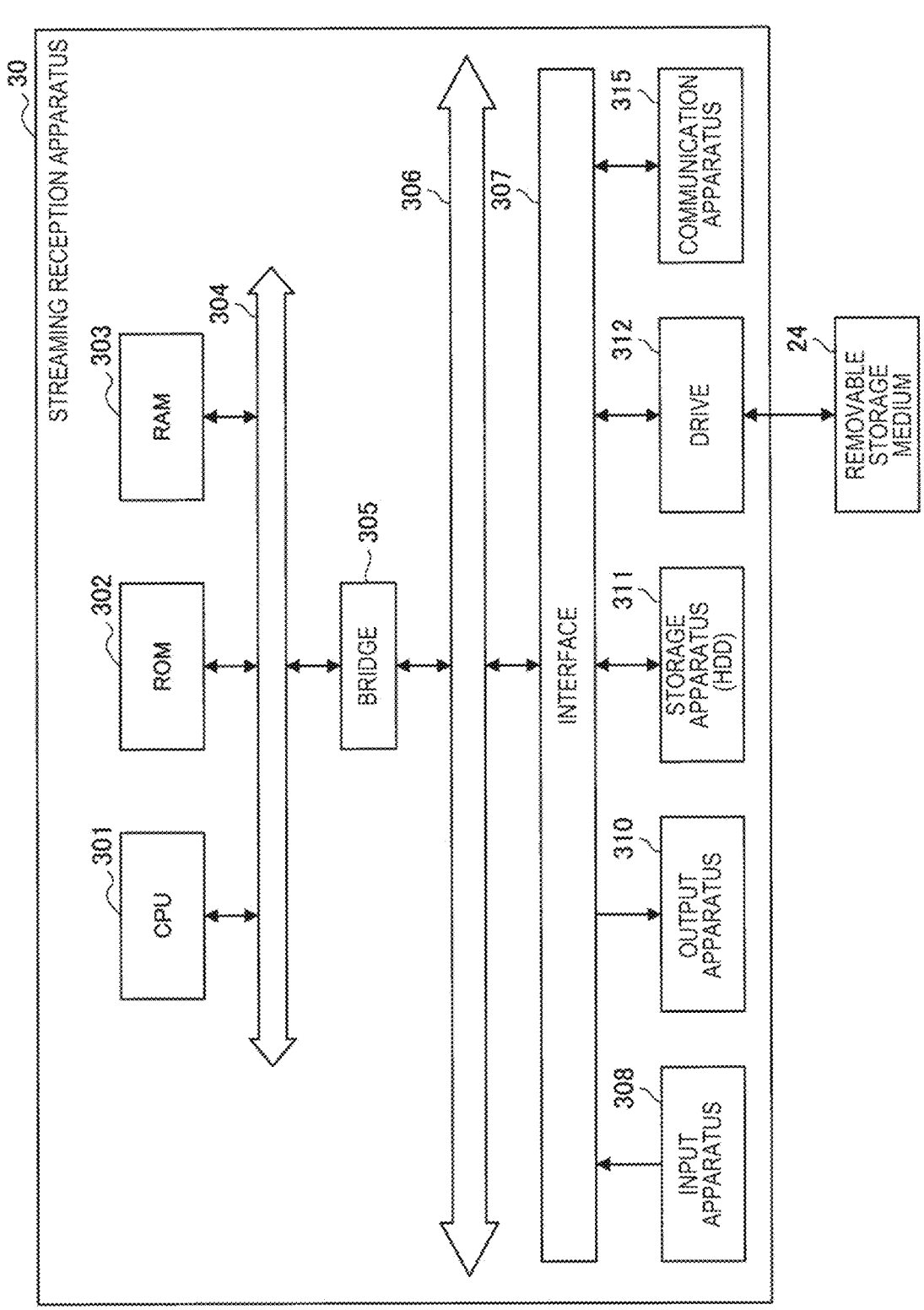
FIG. 19 is a block diagram illustrating a hardware configuration of the streaming reception apparatus.

FIG. 19 is a block diagram illustrating the hardware configuration of the streaming reception apparatus 30. The streaming reception apparatus 30 includes a central processing unit (CPU) 301, a read only memory (ROM) 302, a random access memory (RAM) 303, and a host bus 304. In addition, the streaming reception apparatus 30 includes a bridge 305, an external bus 306, an interface 307, an input apparatus 308, an output apparatus 310, a storage apparatus (HDD) 311, a drive 312, and a communication apparatus 315.

The CPU 301 functions as an operation processing apparatus and a control apparatus, and controls the overall operation of the streaming reception apparatus 30 in accordance with a variety of programs. In addition, the CPU 301 may also be a microprocessor. The ROM 302 stores programs, operation parameters, and the like that the CPU 301 uses. The RAM 303 temporarily stores programs used in the execution of the CPU 301 and the parameters and the like that appropriately change during the execution. These are connected to each other by the host bus 304 including a CPU bus. The cooperation of these CPU 301, ROM 302, and RAM 303 with software can perform the functions of the output control section 320, the main streaming request section 356, and the like described with reference to FIG. 6.

The host bus 304 is connected to the external bus 306 such as a peripheral component interconnect/interface (PCI) bus through the bridge 305. Note that, the host bus 304, the bridge 305, and the external bus 306 are not necessarily configured as different entities, but the functions thereof may be implemented in one bus.

The input apparatus 308 includes an input mechanism such as a mouse, a keyboard, a touch panel, a button, a microphone, a switch, and a lever for a user to input information, and an input control circuit that generates an input signal on the basis of the input from the user and outputs the input signal to the CPU 301. A user of the streaming reception apparatus 30 can input a variety of data to the streaming reception apparatus 30 and instruct the streaming reception apparatus 30 to perform a processing operation by operating the input apparatus 308.

The output apparatus 310 includes, for example, a display apparatus such as a cathode ray tube (CRT) display apparatus, a liquid crystal display (LCD) apparatus, an organic light emitting diode (OLED) apparatus, and a lamp. The output apparatus 310 further includes a sound output apparatus such as a speaker and a headphone. The output apparatus 310 outputs, for example, reproduced content. Specifically, the display apparatus displays various kinds of information such as reproduced video data in the form of text or an image. Meanwhile, the sound output apparatus converts reproduced sound data and the like into a sound, and outputs the sound. Examples of the output apparatus 310 include a personal computer (PC) or an electronic apparatus such as a tablet apparatus. However, the output apparatus 310 may be another apparatus.

The storage apparatus 311 is a data storage apparatus configured as an example of the storage section of the streaming reception apparatus 30 according to the present embodiment. The storage apparatus 311 may include a recording medium, a recording apparatus that records data in the recording medium, a readout apparatus that reads out data from the recording medium, a deletion apparatus that deletes data recoded in the recording medium, and the like. The storage apparatus 311 includes, for example, a hard disk drive (HDD). This storage apparatus 311 drives the hard disk, and stores a program and various kinds of data executed by the CPU 301.

The drive 312 is a reader/writer for a storage medium, and is built in or externally attached to the streaming reception apparatus 30. The drive 312 reads out information recorded on a removable storage medium 24 such as mounted magnetic disks, optical discs, magneto-optical disks and semiconductor memory, and outputs the read-out information to the RAM 303. In addition, the drive 312 can also write information into a removable storage medium 24.

The communication apparatus 315 is, for example, a communication interface including a communication apparatus and the like for a connection to an external apparatus. In addition, the communication apparatus 315 may also be a communication apparatus supporting a wireless local area network (LAN), a communication apparatus supporting Long Term Evolution (LTE), or a wired communication apparatus that performs wired communication.

Note that the above describes the hardware configuration of the streaming reception apparatus 30 with reference to FIG. 19, but the hardware of the streaming transmission apparatus 20 can be configured substantially in the same way as that of the streaming reception apparatus 30. Accordingly, the hardware of the streaming transmission apparatus 20 will not be described.

6. Application Examples

6-1. First Application Example

The technology according to an embodiment of the present disclosure is applicable to a variety of products. For example, the technology according to an embodiment of the present disclosure may be applied to an operating room system.

Figure 20:
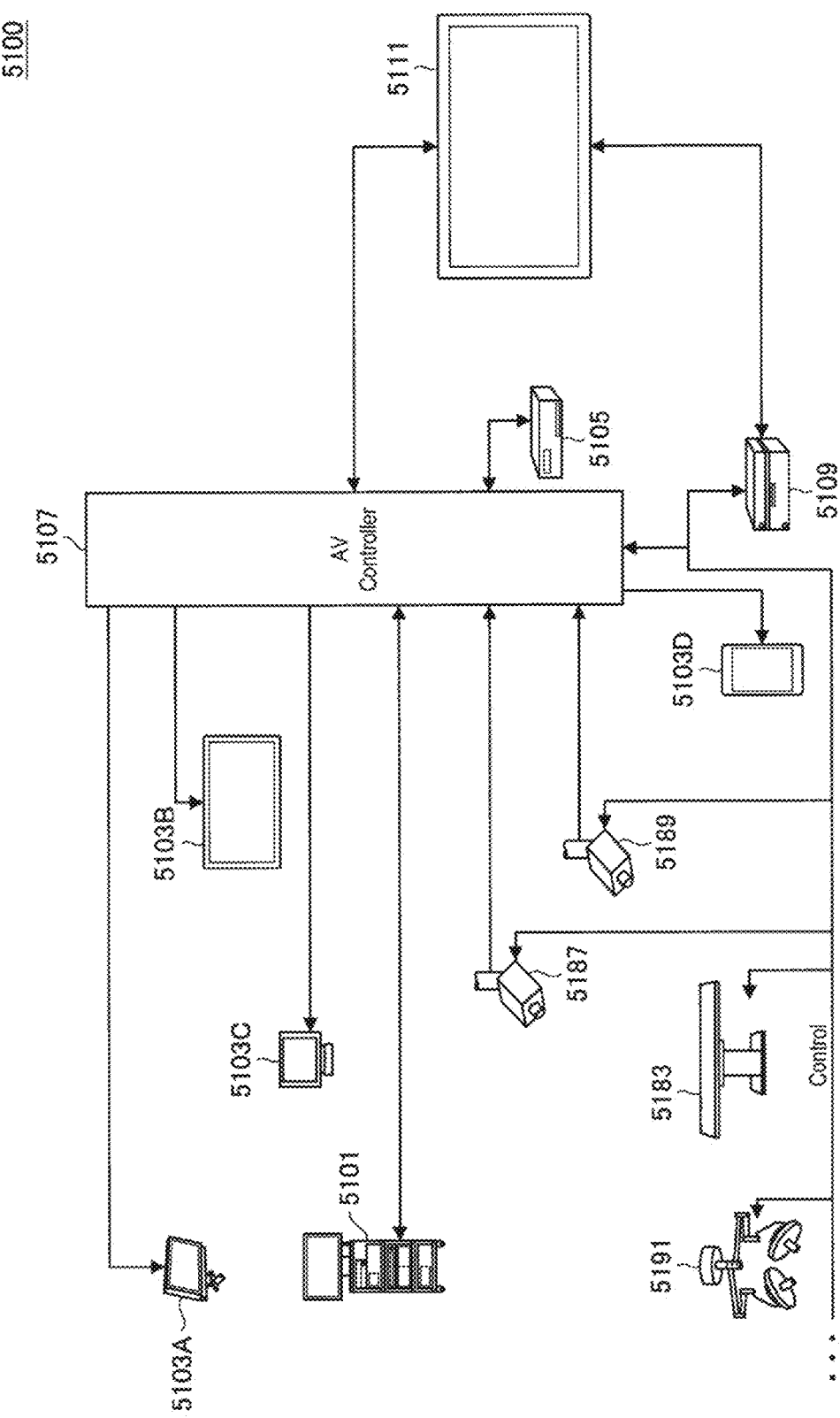
FIG. 20 is a diagram schematically illustrating an overall configuration of an operating room system.

FIG. 20 is a diagram schematically illustrating the overall configuration of an operating room system 5100 to which the technology according to the present disclosure can be applied. Referring to FIG. 20, the operating room system 5100 is configured such that a group of apparatuses installed in an operating room are cooperatively connected to one another via an audiovisual controller (AV controller) 5107 and an operating room control apparatus 5109.

Various apparatuses can be installed in the operating room. As an example, FIG. 20 illustrates a group 5101 of various kinds of apparatuses for endoscopic surgery, a ceiling camera 5187 which is installed on a ceiling of the operating room and images a hand of a surgeon, an operating room camera 5189 which is installed on the ceiling of the operating room and images the state of the entire operating room, a plurality of display apparatuses 5103A to 5103D, a recorder 5105, a patient bed 5183, and lighting 5191.

Here, the apparatus group 5101 among these apparatuses belongs to an endoscopic surgery system 5113 to be described later and includes an endoscope, a display apparatus that displays an image captured by the endoscope, and the like. Each of the apparatuses belonging to the endoscopic surgery system 5113 is also referred to as medical apparatus. On the other hand, the display apparatuses 5103A to 5103D, the recorder 5105, the patient bed 5183, and the lighting 5191 are apparatuses installed separately from, for example, the endoscopic surgery system 5113 in the operating room. Each apparatus not belonging to the endoscopic surgery system 5113 is also referred to as non-medical apparatus. The audiovisual controller 5107 and/or the operating room control apparatus 5109 control the operations of the medical apparatuses and the non-medical apparatuses in cooperation with each other.

The audiovisual controller 5107 controls processing related to image display in the medical apparatuses and the non-medical apparatuses in general. Specifically, the apparatus group 5101, the ceiling camera 5187, and the operating room camera 5189 among the apparatuses included in the operating room system 5100 may be apparatuses (hereinafter referred to as transmission source apparatuses) having a function of transmitting information to be displayed during surgery (hereinafter also referred to as display information). Further, the display apparatuses 5103A to 5103D may be apparatuses from which the display information is output (hereinafter also referred to as output destination apparatuses). Further, the recorder 5105 may be an apparatus corresponding to both the transmission source apparatus and the output destination apparatus. The audiovisual controller 5107 has a function of controlling operations of the transmission source apparatus and the output destination apparatus, acquiring the display information from the transmission source apparatus, and transmitting the display information to the output destination apparatus so that the display information is displayed or recorded. Further, the display information includes various kinds of images captured during the surgery, various kinds of information related to the surgery (for example, body information of a patient, a previous examination result, information related to a surgical form, and the like), and the like.

Specifically, information for an image of a surgery site within a body cavity of the patient imaged by the endoscope can be transmitted from the apparatus group 5101 to the audiovisual controller 5107 as the display information. Further, information for an image of a hand of a surgeon captured by the ceiling camera 5187 can be transmitted from the ceiling camera 5187 as the display information. Further, information for an image illustrating the state of the whole operating room captured by the operating room camera 5189 can be transmitted from the operating room camera 5189 as the display information. Further, in the case where there is another apparatus having an imaging function in the operating room system 5100, the audiovisual controller 5107 may acquire information for an image captured by another apparatus from another apparatus as the display information.

The audiovisual controller 5107 causes the acquired display information (that is, the image captured during the surgery or various kinds of information related to the surgery) to be displayed on at least one of the display apparatuses 5103A to 5103D which are the output destination apparatuses. In the illustrated example, the display apparatus 5103A is a display apparatus which is installed by suspending it from the ceiling of the operating room, the display apparatus 5103B is a display apparatus which is installed on a wall surface of the operating room, the display apparatus 5103C is a display apparatus which is installed on a desk in the operating room, and the display apparatus 5103D is a mobile apparatus (for example, a tablet personnel computer (PC)) having a display function.

Further, although not illustrated in FIG. 20, the operating room system 5100 may include an apparatus outside the operating room. An external apparatus outside the operating room may be, for example, a server connected to a network constructed inside or outside a hospital, a PC used by a medical staff member, a projector installed in a conference room of a hospital, or the like. In the case where the external apparatus is installed outside the hospital, the audiovisual controller 5107 may cause the display information to be displayed on a display apparatus of another hospital via a teleconference system or the like for remote medical care.

The operating room control apparatus 5109 controls processing other than the processing related to image display in the non-medical apparatuses in general. For example, the operating room control apparatus 5109 controls the driving of the patient bed 5183, the ceiling camera 5187, the operating room camera 5189, and the lighting 5191.

A centralized operation panel 5111 is installed in the operating room system 5100, and the user can give an instruction for the image display to the audiovisual controller 5107 via the centralized operation panel 5111 and give an instruction for an operation of the non-medical apparatuses to the operating room control apparatus 5109. The centralized operation panel 5111 is configured such that a touch panel is installed on the display surface of the display apparatus.

FIG. 21 is a diagram illustrating a display example of an operation screen in the centralized operation panel 5111. As an example, an operation screen corresponding to the case where two display apparatuses are installed in the operating room system 5100 as the output destination apparatuses is illustrated in FIG. 21. Referring to FIG. 21, an operation screen 5193 includes a transmission source selection area 5195, a preview area 5197, and a control area 5201.

In the transmission source selection area 5195, the transmission source apparatus installed in the operating room system 5100 and a thumbnail screen indicating the display information stored in the transmission source apparatus are displayed in association with each other. The user can select the display information that she or he desires to display on the display apparatus from any one of the transmission source apparatuses displayed in the transmission source selection area 5195.

In the preview area 5197, previews of screens displayed on the two display apparatuses (Monitor 1 and Monitor 2) which are the output destination apparatuses are displayed. In the illustrated example, four images are displayed in a PinP form on one display apparatus. The four images correspond to the display information transmitted from the transmission source apparatuses selected in the transmission source selection area 5195. One of the four images is displayed with a relatively large size as a main image, and the remaining three images are displayed with a relatively small size as sub-images. The user can perform switching between the main image and the sub-image by appropriately selecting an area in which the four images are displayed. Further, a status display area 5199 is installed below the area in which the four images are displayed, and a status related to surgery (for example, an elapsed time of the surgery, the body information of the patient, or the like) can be appropriately displayed in the area.

A transmission source operation area 5203 in which a graphical user interface (GUI) part for performing an operation on the transmission source apparatus is displayed and an output destination operation area 5205 in which a GUI part for performing an operation on the output destination apparatus is displayed are provided in the control area 5201. In the illustrated example, a GUI part for performing various kinds of operations (panning, tilting, and zooming) on the camera in the transmission source apparatus with the imaging function is provided in the transmission source operation area 5203. The user can operate the operation of the camera in the transmission source apparatus by appropriately selecting the GUI parts. Further, although not illustrated, in the case where the transmission source apparatus selected in the transmission source selection area 5195 is a recorder (that is, in the case where the image which is previously recorded in the recorder is displayed in the preview area 5197), a GUI part for performing an operation such as image reproduction, reproduction stop, rewinding, fast forward, or the like can be provided in the transmission source operation area 5203.

Further, a GUI part for performing various kinds of operations (swapping, flipping, color adjustment, contrast adjustment, and switching between 2D display and 3D display) with respect to display in the display apparatus which is the output destination apparatus is provided in the output destination operation area 5205. The user can operate the display in the display apparatus by appropriately selecting these GUI parts.

Note that, the operation screen displayed on the centralized operation panel 5111 is not limited to the illustrated example, and the user may be able to input an operation on each apparatus which is installed in the operating room system 5100 and can be controlled by the audiovisual controller 5107 and the operating room control apparatus 5109 through the centralized operation panel 5111.

Figure 22:
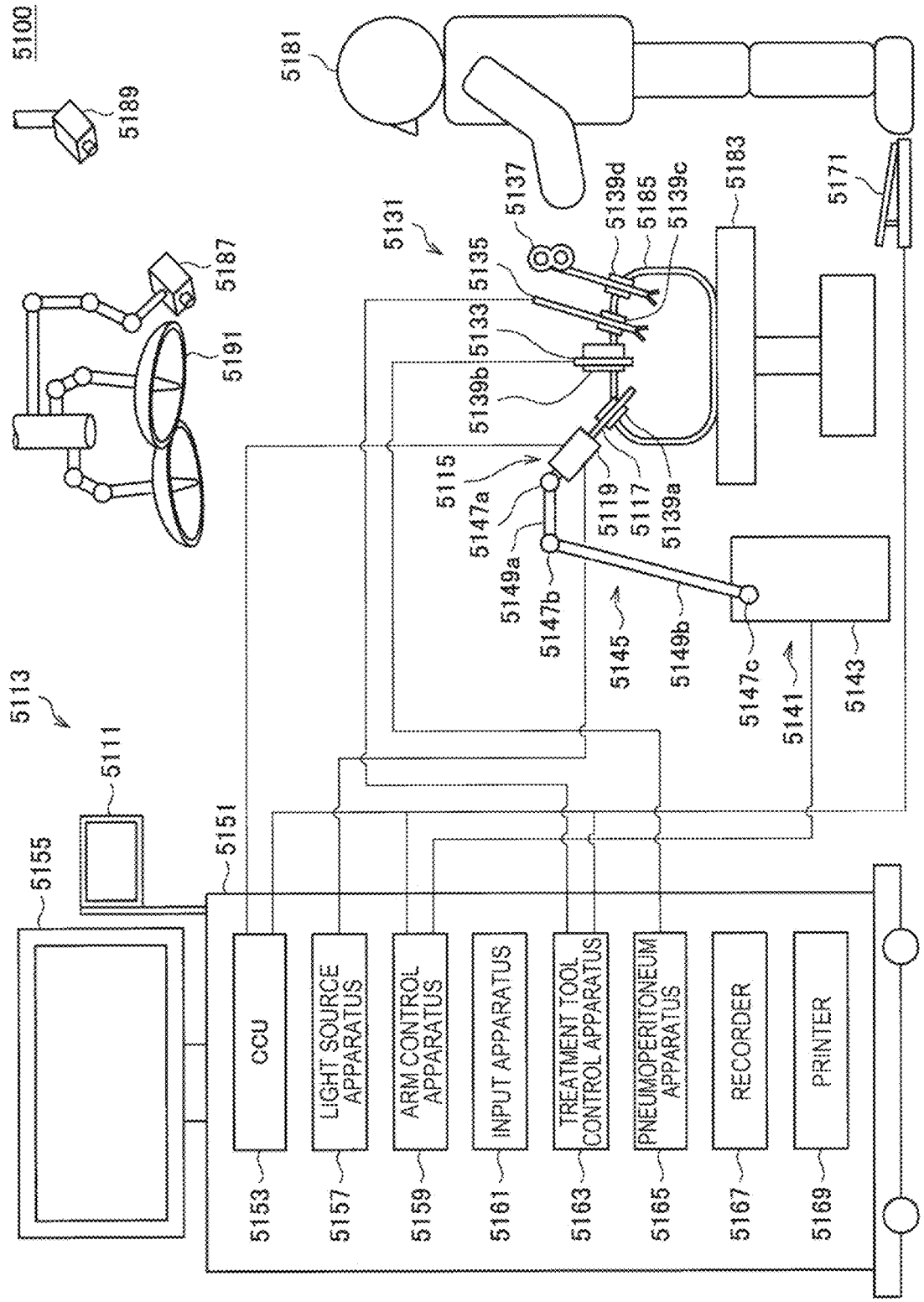
FIG. 22 is a diagram illustrating an example of surgery to which the operating room system is applied.

FIG. 22 is a diagram illustrating an example of the state of surgery to which the operating room system described above is applied. The ceiling camera 5187 and the operating room camera 5189 are installed on the ceiling of the operating room and capable of imaging a hand of a surgeon (physician) 5181 who performs treatment on an affected part of a patient 5185 on the patient bed 5183 and the state of the whole operating room. A magnification adjustment function, a focal length adjustment function, an imaging direction adjustment function, and the like may be provided in the ceiling camera 5187 and the operating room camera 5189. The lighting 5191 is installed on the ceiling of the operating room and illuminates at least the hand of the surgeon 5181. The lighting 5191 may be capable of appropriately adjusting an irradiation light amount, a wavelength (color) of irradiation light, a light irradiation direction, and the like.

As illustrated in FIG. 20, the endoscopic surgery system 5113, the patient bed 5183, the ceiling camera 5187, the operating room camera 5189, and the illumination 5191 are cooperatively connected to one another via the audiovisual controller 5107 and the operating room control apparatus 5109 (not illustrated in FIG. 22). The centralized operation panel 5111 is installed in the operating room, and as described above, the user can appropriately operate these apparatuses installed in the operating room through the centralized operation panel 5111.

Hereinafter, the configuration of the endoscopic surgery system 5113 will be described in detail. As illustrated in the diagram, the endoscopic surgery system 5113 includes an endoscope 5115, other surgical instruments 5131, a support arm apparatus 5141 that supports the endoscope 5115, and a cart 5151 on which various apparatuses for endoscopic surgery are provided.

In endoscopic surgery, instead of opening up the abdomen by cutting the abdominal wall, tubular hole-opening tools called trocars 5139a to 5139d are used to puncture the abdominal wall in a plurality of places. Subsequently, the lens tube 5117 of the endoscope 5115 and other surgical instruments 5131 are inserted into the body cavity of the patient 5185 from the trocars 5139a to 5139d. In the illustrated example, a pneumoperitoneum tube 5133, an energy treatment tool 5135, and forceps 5137 are inserted into the body cavity of the patient 5185 as the other surgical instruments 5131. The energy treatment tool 5135 is a treatment tool that makes incisions into and ablates tissues, or seals blood vessels or the like, with a high-frequency electric current or ultrasonic vibration. However, the surgical instruments 5131 illustrated in the diagram are merely an example, and any of various types of surgical instruments typically used in endoscopic surgery, such as tweezers and retractors, for example, may also be used as the surgical instruments 5131.

An image of the operating site inside the body cavity of the patient 5185 taken by the endoscope 5115 is displayed on a display apparatus 5155. The surgeon 5181 uses the energy treatment tool 5135 and the forceps 5137 to perform treatments, such as excising an affected area, for example, while viewing in real-time the image of the operating site displayed on the display apparatus 5155. Note that, although omitted from the diagram, the pneumoperitoneum tube 5133, the energy treatment tool 5135, and the forceps 5137 are supported by a person such as the surgeon 5181 or an assistant during surgery.

(Support Arm Apparatus)

The support arm apparatus 5141 is provided with an arm section 5145 that extends from a base section 5143. In the illustrated example, the arm section 5145 includes joint sections 5147a, 5147b, and 5147c, as well as links 5149a and 5149b, and is driven by control commands from the arm control apparatus 5159. The endoscope 5115 is supported by the arm section 5145, with the position and attitude controlled thereby. With this arrangement, locking of the endoscope 5115 in a stable position may be realized.

(Endoscope)

The endoscope 5115 includes a lens tube 5117 having a region of certain length from the front end that is inserted into the body cavity of the patient 5185, and a camera head 5119 connected to the base end of the lens tube 5117. In the example illustrated in the diagram, an endoscope 5115 configured as a so-called rigid scope having a rigid lens tube 5117 is illustrated, but the endoscope 5115 may also be configured as a so-called flexible scope having the flexible lens tube 5117.

On the front end of the lens tube 5117, there is provided an opening into which an objective lens is fitted. A light source apparatus 5157 is connected to the endoscope 5115. Light generated by the light source apparatus 5157 is guided up to the front end of the lens tube 5117 by a light guide extending inside the lens tube 5117, and is radiated through the objective lens towards an observation target inside the body cavity of the patient 5185. Note that the endoscope 5115 may be a forward-viewing scope, an oblique-viewing scope, or a side-viewing scope.

An optical system and an image sensor are provided inside the camera head 5119, and reflected light from the observation target (observation light) is condensed onto the image sensor by the optical system. Observation light is photoelectrically converted by the image sensor, and an electrical signal corresponding to the observation light, or in other words, an image signal corresponding to the observed image, is generated. The image signal is transmitted as RAW data to a camera control unit (CCU) 5153. Note that the camera head 5119 is provided with a function of adjusting the magnification and the focus distance by appropriately driving the optical system.

Note that, to support stereoscopic vision (3D display) or the like, for example, the camera head 5119 may also be provided with a plurality of image sensors. In this case, a plurality of relay optical subsystems are provided inside the lens tube 5117 to guide the observation light to each of the plurality of image sensors.

(Various Devices Provided on Cart)

The CCU 5153 includes components such as a central processing unit (CPU) and a graphics processing unit (GPU), and centrally controls the operations of the endoscope 5115 and the display apparatus 5155. Specifically, the CCU 5153 subjects an image signal received from the camera head 5119 to various types of image processing for displaying an image based on the image signal, such as development processing (demosaic processing), for example. The CCU 5153 provides an image signal that has been subjected to such image processing to the display apparatus 5155. Further, the audiovisual controller 5107 illustrated in FIG. 20 is connected to a CCU 5153. The CCU 5153 also provides an image signal which has undergone image processing to the audiovisual controller 5107. Also, the CCU 5153 transmits a control signal to the camera head 5119 to control the driving thereof. The control signal may include information related to imaging parameters, such as the magnification and focus distance. Information related to imaging parameters may be input via an input apparatus 5161 or may be input via the centralized operation panel 5111.

The display apparatus 5155, under control by the CCU 5153, displays an image based on an image signal subjected to image processing by the CCU 5153. In the case where the endoscope 5115 supports imaging at high resolution such as 4K (3840 horizontal pixels*2160 vertical pixels) or 8K (7680 horizontal pixels×4320 vertical pixels), and/or supports 3D display, for example, an apparatus compatible with each and capable of high-resolution display and/or capable of 3D display may be used as the display apparatus 5155. In the case where imaging at high resolution such as 4K or 8K is supported, an apparatus with a size of 55 inches or more may be used as the display apparatus 5155 to thereby obtain an even deeper sense of immersion. Also, depending on the application, a plurality of display apparatuses 5155 at different resolutions and sizes may also be provided.

The light source apparatus 5157 includes a light source such as a light-emitting diode (LED), for example, and supplies the endoscope 5115 with irradiating light when imaging the operating site.

An arm control apparatus 5159 includes a processor such as a CPU, for example, and by operating in accordance with a certain program, controls the driving of the arm section 5145 of the support arm apparatus 5141 in accordance with a certain control method.

An input apparatus 5161 is an input interface with respect to the endoscopic surgery system 5113. Through the input apparatus 5161, the user is able to input various kinds of information and instructions into the endoscopic surgery system 5113. For example, through the input apparatus 5161, the user inputs various kinds of information related to surgery, such as physical information about the patient, and information about surgical procedures. As another example, through the input apparatus 5161, the user inputs instructions to drive the arm section 5145, instructions to change the imaging parameters of imaging by the endoscope 5115 (such as the type of irradiating light, the magnification, and the focus distance), instructions to drive the energy treatment tool 5135, and the like.

The type of the input apparatus 5161 is not limited, and the input apparatus 5161 may be any of various known types of input apparatuses. For example, apparatuses such as a mouse, a keyboard, a touch panel, a switch, a footswitch 5171, and/or a lever may be applied as the input apparatus 5161. In the case where a touch panel is used as the input apparatus 5161, the touch panel may be provided on the display screen of the display apparatus 5155.

Alternatively, the input apparatus 5161 is an apparatus worn by the user, such as an eyeglasses-style wearable apparatus or a head-mounted display (HMD), for example, and various inputs are performed in accordance with the user's gestures or gaze detected by these apparatuses. Also, the input apparatus 5161 includes a camera able to detect the user's movement, and various inputs are performed in accordance with the user's gestures or gaze detected from a video captured by the camera. Furthermore, the input apparatus 5161 includes a microphone able to pick up the user's voice, and various inputs are performed by voice via the microphone. In this way, by configuring the input apparatus 5161 to be capable of accepting the input of various types of information in a non-contact manner, a user belonging to a clean area in particular (for example, the surgeon 5181) becomes able to operate an apparatus belonging to an unclean area in a non-contact manner. Also, since the user becomes able to operate an apparatus without taking one's hands away from the tools the user is holding, user convenience is improved.

A treatment tool control apparatus 5163 controls the driving of the energy treatment tool 5135 to cauterize or make incisions into tissue, seal blood vessels, or the like. The pneumoperitoneum apparatus 5165 delivers gas into the body cavity through the pneumoperitoneum tube 5133 to inflate the body cavity of the patient 5185 for the purpose of securing a field of view for the endoscope 5115 and securing a workspace for the surgeon. The recorder 5167 is an apparatus capable of recording various types of information related to surgery. The printer 5169 is an apparatus capable of printing out various types of information related to surgery in various formats, such as text, images, or graphs.

A particularly characteristic configuration in the endoscopic surgery system 5113 will be described below in more detail.

(Support Arm Apparatus)

The support arm apparatus 5141 includes a base section 5143 which acts as a base, and an arm section 5145 which extends from the base section 5143. In the illustrated example, the arm section 5145 includes a plurality of joint sections 5147a, 5147b, and 5147c, as well as a plurality of links 5149a and 5149b joined by the joint section 5147b, but in FIG. 22, for the sake of simplicity, the configuration of the arm section 5145 is illustrated in a simplified manner. In actuality, factors such as the shapes, numbers, and arrangement of the joint sections 5147a to 5147c and the links 5149a and 5149b, and the directions of the rotation axes of the joint sections 5147a to 5147c may be set appropriately so that the arm section 5145 has the desired degrees of freedom. For example, the arm section 5145 preferably may be configured to have six or more degrees of freedom. With this arrangement, it is possible to move the endoscope 5115 freely within the movable range of the arm section 5145, and thus it becomes possible to insert the lens tube 5117 of the endoscope 5115 into the body cavity of the patient 5185 from a desired direction.

The joint sections 5147a to 5147c include an actuator, and the joint sections 5147a to 5147c are configured to be rotatable about a certain rotation axis in accordance with the driving of the actuator. By controlling the driving of the actuator with the arm control apparatus 5159, the rotational angle of each of the joint sections 5147a to 5147c is controlled, and the driving of the arm section 5145 is controlled. With this arrangement, control of the position and the attitude of the endoscope 5115 may be realized. At this point, the arm control apparatus 5159 is able to control the driving of the arm section 5145 with any of various known types of control methods, such as force control or position control.

For example, by having the surgeon 5181 perform appropriate operation input via the input apparatus 5161 (including the footswitch 5171), the driving of the arm section 5145 may be controlled appropriately by the arm control apparatus 5159 in accordance with the operation input, and the position and the attitude of the endoscope 5115 may be controlled. By such control, after moving the endoscope 5115 on the front end of the arm section 5145 from an arbitrary position to an arbitrary position, the endoscope 5115 can be supported securely at the new position. Note that the arm section 5145 may also be operated by what is called a master-slave method. In this case, the arm section 5145 may be operated remotely by a user via the input apparatus 5161 installed in a location distant from the operating room.

Also, in the case where force control is applied, the arm control apparatus 5159 may receive external force from the user, and drive the actuator of each of the joint sections 5147a to 5147c so that the arm section 5145 moves smoothly in response to the external force, also known as power assist control. With this arrangement, when the user moves the arm section 5145 while touching the arm section 5145 directly, the arm section 5145 can be moved with comparatively light force. Consequently, it becomes possible to move the endoscope 5115 more intuitively with a simpler operation, and user convenience can be improved.

Herein, in endoscopic surgery, typically the endoscope 5115 has been supported by a doctor called a scopist. In contrast, by using the support arm apparatus 5141, it becomes possible to keep the position of the endoscope 5115 fixed more reliably without manual work, and thus image of the operating site can be obtained consistently, making it possible to perform surgery smoothly.

Note that the arm control apparatus 5159 does not necessarily have to be provided on the cart 5151. Also, the arm control apparatus 5159 does not necessarily have to be one apparatus. For example, the arm control apparatus 5159 may also be proved respectively in each of the joint sections 5147a to 5147c of the arm section 5145 of the support arm apparatus 5141, and the plurality of arm control apparatuses 5159 may cooperate with each other to realize driving control of the arm section 5145.

(Light Source Apparatus)

The light source apparatus 5157 supplies the endoscope 5115 with irradiating light when imaging the operating site. The light source apparatus 5157 includes a white light source configured by an LED, a laser light source, or a combination of the two, for example. At this point, in the case where the white light source is configured by a combination of RGB laser light sources, the output intensity and output timing of each color (each wavelength) can be controlled with high precision, and thus the white balance of the captured image can be adjusted with the light source apparatus 5157. Also, in this case, by irradiating the observation target with laser light from each of the RGB laser light sources in a time-division manner, and controlling the driving of the image sensor of the camera head 5119 in synchronization with the irradiation timings, it is also possible to capture images corresponding to R, G, and B, respectively, in a time-division manner. According to such a method, color images can be obtained without providing the image sensor with a color filter.

Also, the driving of the light source apparatus 5157 may also be controlled so as to change the intensity of the light to output every time a certain amount of time elapses. By controlling the driving of the image sensor of the camera head 5119 in synchronization with the timings of changing the light intensity to acquire images in a time-division manner, and compositing the images together, it is possible to generate a high dynamic range image without what are called crushed blacks and blown-out whites.

Additionally, the light source apparatus 5157 may also be configured to be able to supply light in a certain wavelength band corresponding to special imaging. With special imaging, for example, the wavelength dependency of light absorption by tissues of the body is utilized, and light is radiated in a narrow band compared to the irradiating light during normal observation (that is, white light) to thereby image certain tissues, such as blood vessels in the superficial portion of the mucous membrane, at a high contrast, also known as narrow band imaging (NBI). Alternatively, with special imaging, fluorescent observation that obtains an image with fluorescent light by radiating excitation light may also be conducted. With fluorescent observation, it is possible to irradiate a body tissue with excitation light and observe fluorescent light from the body tissue (autofluorescence observation), or locally inject a reagent such as indocyanine green (ICG) into a body tissue while also irradiating that body tissue with excitation light corresponding to the fluorescence wavelength of the reagent to obtain a fluorescent image, or the like. The light source apparatus 5157 may be configured to be able to supply narrow-band light and/or excitation light corresponding to such special imaging.

(Camera Head and CCU)

Figure 23:
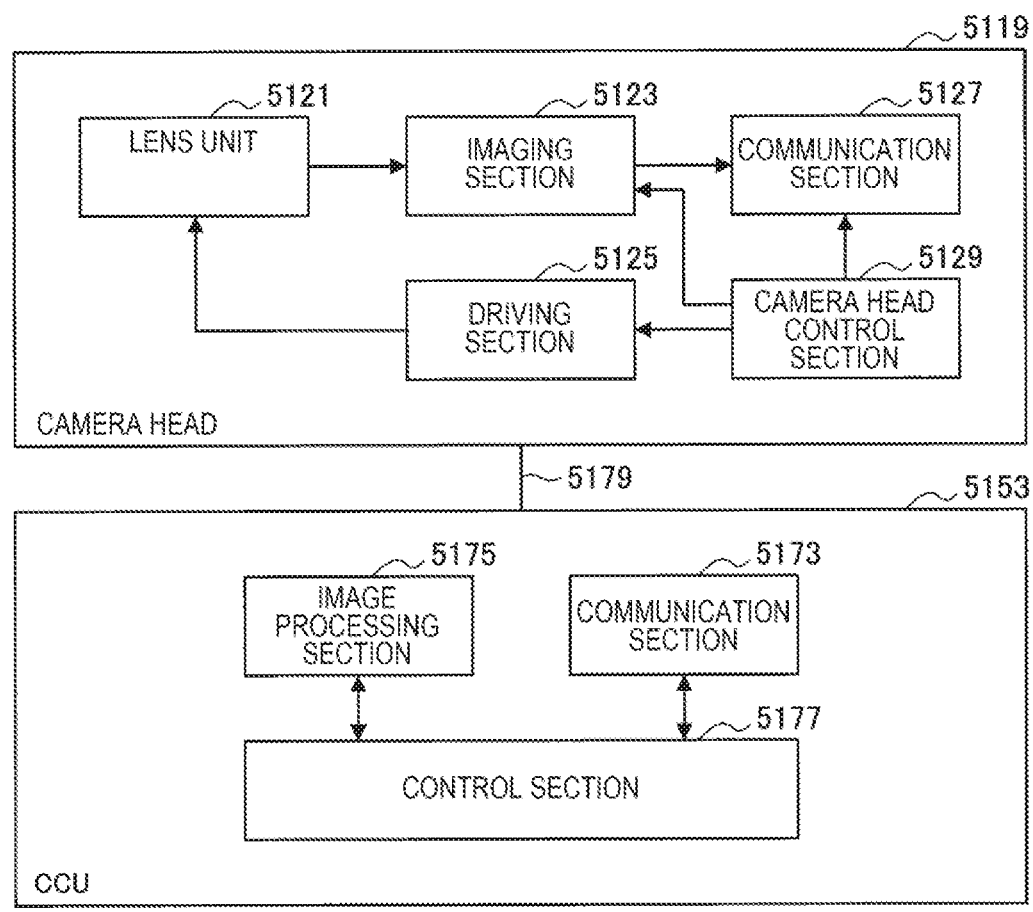
FIG. 23 is a block diagram illustrating an example of functional components of a camera head and a CCU illustrated in FIG. 22.

The functions of the camera head 5119 and the CCU 5153 of the endoscope 5115 will be described in more detail with reference to FIG. 23. FIG. 23 is a block diagram illustrating an example of functional components of the camera head 5119 and the CCU 5153 illustrated in FIG. 22.

Referring to FIG. 23, functionally, the camera head 5119 includes a lens unit 5121, an imaging section 5123, a driving section 5125, a communication section 5127, and a camera head control section 5129. Also, functionally, the CCU 5153 includes a communication section 5173, an image processing section 5175, and a control section 5177. The camera head 5119 and the CCU 5153 are bidirectionally communicably connected by a transmission cable 5179.

First, a functional component of the camera head 5119 will be described. The lens unit 5121 is an optical system provided in the part that connects to the lens tube 5117. Observation light taken in from the front end of the lens tube 5117 is guided up to the camera head 5119, and is incident on the lens unit 5121. The lens unit 5121 includes a combination of a plurality of lenses, including a zoom lens and a focus lens. The optical characteristics of the lens unit 5121 are adjusted to condense observation light onto the photosensitive face of an image sensor in the imaging section 5123. Also, the zoom lens and the focus lens are configured to be able to move position on the optical axis to adjust the magnification and the focus of the captured image.

The imaging section 5123 includes an image sensor, and is disposed downstream from the lens unit 5121. Observation light passing through the lens unit 5121 is condensed onto the photosensitive face of the image sensor, and by photoelectric conversion, an image signal corresponding to the observed image is generated. The image signal generated by the imaging section 5123 is provided to the communication section 5127.

For the image sensor included in the imaging section 5123, a complementary metal-oxide semiconductor (CMOS) type image sensor having a Bayer array to enable color imaging is used, for example. Note that a sensor capable of capturing high-resolution images of 4K or greater may be used as the image sensor, for example. By obtaining a high-resolution image of the operating site, the surgeon 5181 becomes able to grasp the state of the operating site in more detail, and proceed with surgery more smoothly.

Also, the image sensor included in the imaging section 5123 includes a pair of image sensors for respectively acquiring image signals for the right eye and the left eye corresponding to 3D display. By presenting a 3D display, the surgeon 5181 becomes able to grasp the depth of biological tissue at the operating site more accurately. Note that if the imaging section 5123 has a multi-chip configuration, the lens unit 5121 likewise is provided with a plurality of subsystems corresponding to each of the image sensors.

Also, the imaging section 5123 is not necessarily provided in the camera head 5119. For example, the imaging section 5123 may also be provided inside the lens tube 5117, directly behind the objective lens.

The driving section 5125 includes actuators, and under control from the camera head control section 5129, moves the zoom lens and the focus lens of the lens unit 5121 by a certain distance along the optical axis. With this arrangement, the magnification and the focus of the image captured by the imaging section 5123 may be adjusted appropriately.

The communication section 5127 includes a communication apparatus for transmitting and receiving various kinds of information to and from the CCU 5153. The communication section 5127 transmits an image signal obtained from the imaging section 5123 as RAW data to the CCU 5153 through the transmission cable 5179. At this point, to display the captured image of the operating site with low latency, the image signal preferably is transmitted by optical communication. This is because during surgery, the surgeon 5181 performs surgery while observing the state of the affected area via the captured image, and thus for safer and more reliable surgery, there is demand for the moving image of the operating site to be displayed as close to real-time as possible. In the case where optical communication is conducted, the communication section 5127 is provided with a photoelectric conversion module that converts an electrical signal into an optical signal. The image signal is converted into an optical signal by the photoelectric conversion module, and then transmitted to the CCU 5153 through the transmission cable 5179.

Also, the communication section 5127 receives from the CCU 5153 a control signal for controlling the driving of the camera head 5119. The control signal includes information related to imaging parameters, such as information specifying the frame rate of the captured image, information specifying the exposure value during imaging, and/or information specifying the magnification and focus of the captured image, for example. The communication section 5127 provides the received control signal to the camera head control section 5129. Note that the control signal from the CCU 5153 may also be transmitted by optical communication. In this case, the communication section 5127 is provided with a photoelectric conversion module that converts an optical signal into an electrical signal, whereby the control signal is converted into an electrical signal by the photoelectric conversion module, and then provided to the camera head control section 5129.

Note that the above imaging parameters such as the frame rate, the exposure value, the magnification, and the focus are set automatically by the control section 5177 of the CCU 5153 on the basis of the acquired image signal. In other words, what are called an auto exposure (AE) function, an auto focus (AF) function, and an auto white balance (AWB) function are provided in the endoscope 5115.

The camera head control section 5129 controls the driving of the camera head 5119 on the basis of a control signal from the CCU 5153 received via the communication section 5127. For example, the camera head control section 5129 controls the driving of the image sensor of the imaging section 5123, on the basis of information specifying the frame rate of the captured image and/or information specifying the exposure during imaging. As another example, the camera head control section 5129 appropriately moves the zoom lens and the focus lens of the lens unit 5121 via the driving section 5125, on the basis of information specifying the magnification and the focus of the captured image. Additionally, the camera head control section 5129 may also be provided with a function of storing information for identifying the lens tube 5117 and the camera head 5119.

Note that, by disposing parts of the components such as the lens unit 5121 and the imaging section 5123 in a highly airtight and waterproof sealed structure, the camera head 5119 can be made to withstand autoclaving sterilization processing.

Next, a functional component of the CCU 5153 will be described. The communication section 5173 includes a communication apparatus for transmitting and receiving various kinds of information to and from the camera head 5119. The communication section 5173 receives an image signal transmitted from the camera head 5119 through the transmission cable 5179. At this point, as described earlier, the image signal preferably may be transmitted by optical communication. In this case, to support optical communication, the communication section 5173 is provided with a photoelectric conversion module that converts an optical signal into an electrical signal. The communication section 5173 provides the image signal converted into an electrical signal to the image processing section 5175.

Also, the communication section 5173 transmits a control signal for controlling the driving of the camera head 5119 to the camera head 5119. The control signal may also be transmitted by optical communication.

The image processing section 5175 performs various types of image processing on the image signal including RAW data transmitted from the camera head 5119. The image processing includes various types of established signal processing, such as development processing, image quality-improving processing (such as band enhancement processing, super-resolution processing, noise reduction (NR) processing, and/or shake correction processing), and/or enlargement processing (digital zoom processing), for example. Also, the image processing section 5175 conducts wave detection processing on the image signal to conduct AE, AF, and AWB.

The image processing section 5175 includes a processor such as a CPU or GPU, and by having the processor operate in accordance with a certain program, the image processing and wave detection processing described above may be conducted. Note that, in the case where the image processing section 5175 includes a plurality of GPUs, the image processing section 5175 appropriately divides up information related to the image signal, and conducts image processing in parallel with the plurality of GPUs.

The control section 5177 performs various kinds of control related to the imaging of the operating site by the endoscope 5115 and the display of a captured image therefrom. For example, the control section 5177 generates a control signal for controlling the driving of the camera head 5119. At this point, in the case where imaging parameters are input by the user, the control section 5177 generates a control signal on the basis of the input by the user. Alternatively, in the case where the endoscope 5115 is provided with an AE function, an AF function, and an AWB function, the control section 5177 appropriately computes an optimal exposure value, focus distance, and white balance in accordance with the results of the wave detection processing by the image processing section 5175, and generates a control signal.

In addition, the control section 5177 causes the display apparatus 5155 to display an image of the operating site on the basis of the image signal subjected to image processing by the image processing section 5175. At this point, the control section 5177 uses any of various types of image recognition technology to recognize various objects in the operating site image. For example, by detecting features such as the edge shapes and colors of objects included in the operating site image, the control section 5177 is able to recognize surgical instruments such as forceps, a specific site of the body, hemorrhaging, mist during usage of the energy treatment tool 5135, and the like. When causing the display apparatus 5155 to display an image of the operating site, the control section 5177 uses the recognition results to overlay various surgical assistance information onto the image of the operating site. By overlaying and providing the surgeon 5181 with surgical assistance information, it becomes possible to proceed with surgery more safely and reliably.

The transmission cable 5179 that connects the camera head 5119 and the CCU 5153 is an electrical signal cable supporting the communication of electrical signals, optical fiber supporting optical communication, or a composite cable of the above.

At this point, in the illustrated example, communication is conducted in a wired manner using the transmission cable 5179, but communication between the camera head 5119 and the CCU 5153 may also be conducted wirelessly. In the case where the communication between the two is conducted wirelessly, it is no longer necessary to lay down the transmission cable 5179 inside the operating room, and thus a situation in which the movement of medical staff inside the operating room is impeded by the transmission cable 5179 may be resolved.

The example of the operating room system 5100 to which the technology according to an embodiment of the present disclosure can be applied has been described above. Further, the case where a medical system to which the operating room system 5100 is applied is the endoscopic surgery system 5113 has been here described as an example, but the configuration of the operating room system 5100 is not limited to this example. For example, the operating room system 5100 may be applied to a flexible endoscope system for inspection or a microscopic surgery system instead of the endoscopic surgery system 5113.

The technology according to an embodiment of the present disclosure relates to the above-described operating room system, and can be applied to grasp the situation of the operating room. Specifically, the operating room camera 5189 corresponds to the streaming transmission apparatus 20. The display apparatus 5103 corresponds to the display apparatus 40. The audiovisual controller 5107 or the operating room control apparatus 5109 corresponds to the streaming reception apparatus 30. In this case, a user may select a sub-video displayed as a thumbnail screen to transmit a main streaming transmission start request. Alternatively, a main streaming transmission start request may be transmitted to any of the operating room cameras 5189 in accordance with sensing information of a patient. For example, in the case where an electrocardiogram of a patient shows abnormality, a main streaming transmission start request may be transmitted to the operating room camera 5189 that images a site related to the electrocardiogram.

6-2. Second Application Example

In addition, the technology according to an embodiment of the present disclosure is implemented as apparatuses mounted on any type of mobile objects such as automobiles, electric vehicles, hybrid electric vehicles, motorcycles, bicycles, personal mobilities, airplanes, drones, ships, robots, construction machines, and agricultural machines (tractors).

Figure 24:
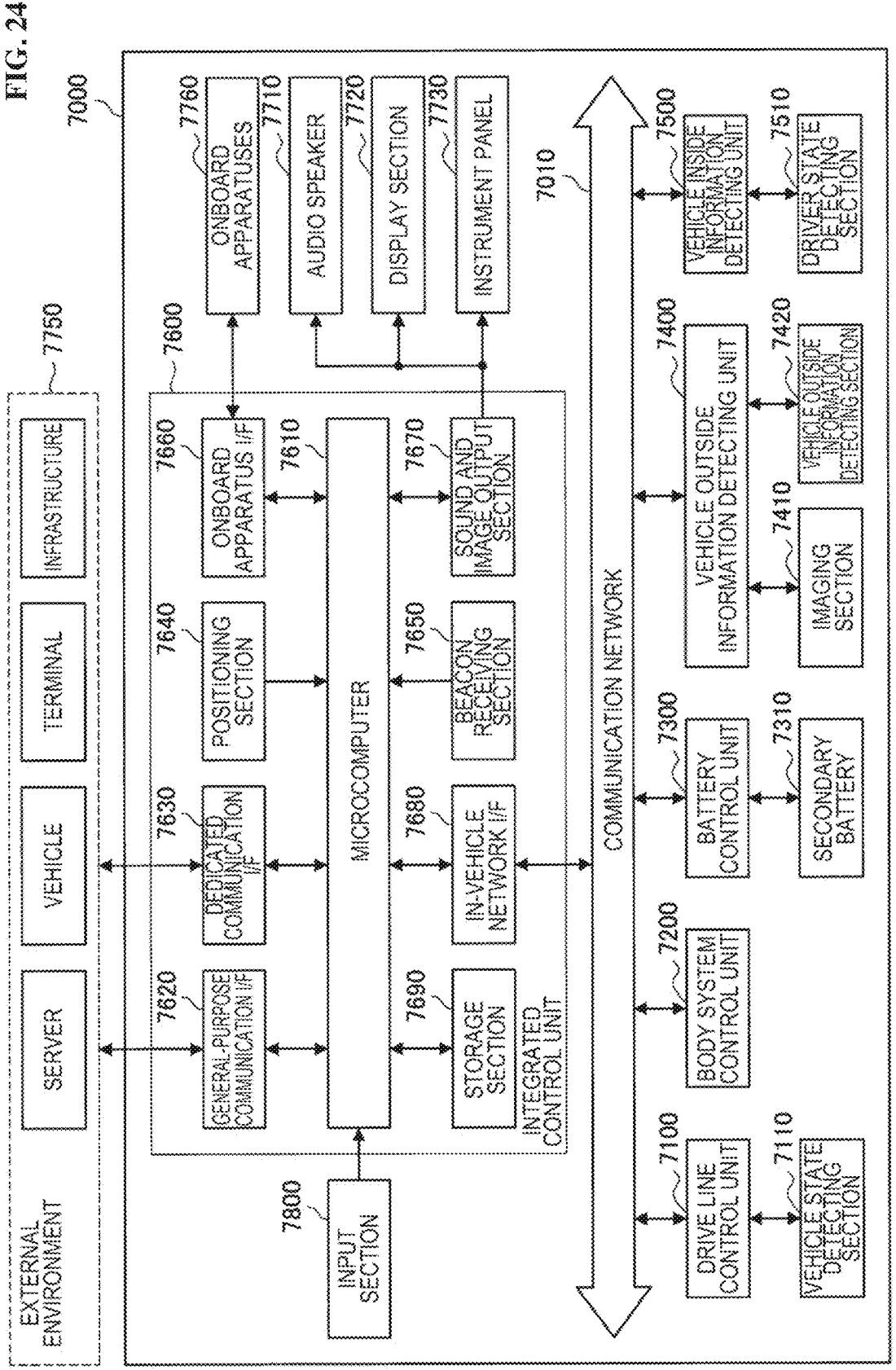
FIG. 24 is a block diagram illustrating an example of a schematic configuration of a vehicle control system.

FIG. 24 is a block diagram illustrating a schematic configuration example of a vehicle control system 7000 that is an example of a mobile object control system to which the technology according to an embodiment of the present disclosure can be applied. The vehicle control system 7000 includes a plurality of electronic control units connected via a communication network 7010. In the example illustrated in FIG. 24, the vehicle control system 7000 includes a drive line control unit 7100, a body system control unit 7200, a battery control unit 7300, a vehicle outside information detecting unit 7400, a vehicle inside information detecting unit 7500, and an integrated control unit 7600. The communication network 7010, which connects these control units, may be an in-vehicle communication network such as a controller area network (CAN), a local interconnect network (LIN), a local area network (LAN), or FlexRay (registered trademark) that is compliant with any standard.

Each control unit includes a microcomputer that performs operation processing in accordance with a variety of programs, a storage section that stores the programs, parameters used for the variety of operations, or the like executed by the microcomputer, and a driving circuit that drives apparatuses subjected to various kinds of control. Each control unit includes a network I/F used to communicate with the other control units via the communication network 7010, and a communication I/F used to communicate with apparatuses, sensors, or the like outside and inside the vehicle through wired communication or wireless communication. FIG. 24 illustrates a microcomputer 7610, a general-purpose communication I/F 7620, a dedicated communication I/F 7630, a positioning section 7640, a beacon receiving section 7650, an onboard apparatus I/F 7660, an audio and image output section 7670, an in-vehicle network I/F 7680, and a storage section 7690 as functional components of the integrated control unit 7600. Each of the other control units similarly includes a microcomputer, a communication I/F, a storage section, and the like.

The drive line control unit 7100 controls the operations of apparatuses related to the drive line of the vehicle in accordance with a variety of programs. For example, the drive line control unit 7100 functions as a control apparatus for a driving force generating apparatus such as an internal combustion engine or a driving motor that generates the driving force for the vehicle, a driving force transferring mechanism that transfers the driving force to wheels, a steering mechanism that adjusts the steering angle of the vehicle, a braking apparatus that generates the braking force for the vehicle, and the like. The drive line control unit 7100 may have the function of a control apparatus for an antilock brake system (ABS) or an electronic stability control (ESC).

The drive line control unit 7100 is connected to a vehicle state detecting section 7110. The vehicle state detecting section 7110 includes, for example, at least one of sensors such as a gyro sensor that detects the angular velocity of the axial rotating motion of the vehicle body, an acceleration sensor that detects the acceleration of the vehicle, or a sensor that detects the operation amount of the accelerator pedal, the operation amount of the brake pedal, the steering wheel angle of the steering wheel, the engine speed, the wheel rotation speed, or the like. The drive line control unit 7100 uses a signal input from the vehicle state detecting section 7110 to perform operation processing, and controls the internal combustion engine, the driving motors, the electric power steering apparatus, the braking apparatus, or the like.

The body system control unit 7200 controls the operations of a variety of apparatuses attached to the vehicle body in accordance with a variety of programs. For example, the body system control unit 7200 functions as a control apparatus for a keyless entry system, a smart key system, a power window apparatus, or a variety of lights such as a headlight, a backup light, a brake light, a blinker, or a fog lamp. In this case, the body system control unit 7200 can receive radio waves transmitted from a portable apparatus that serves instead of the key or signals of a variety of switches. The body system control unit 7200 receives these radio waves or signals, and controls the vehicle door lock apparatus, the power window apparatus, the lights, or the like.

The battery control unit 7300 controls a secondary battery 7310 in accordance with a variety of programs. The secondary battery 7310 serves as a power supply source of a driving motor. For example, the battery control unit 7300 receives information such as the battery temperature, the battery output voltage, or the remaining battery capacity from a battery apparatus including the secondary battery 7310. The battery control unit 7300 uses these signals to perform operation processing, and performs temperature adjusting control on the secondary battery 7310 or controls a cooling apparatus or the like included in the battery apparatus.

The vehicle outside information detecting unit 7400 detects information on the outside of the vehicle including the vehicle control system 7000. For example, the vehicle outside information detecting unit 7400 is connected to at least one of an imaging section 7410 and a vehicle outside information detecting section 7420. The imaging section 7410 includes at least one of a time of flight (ToF) camera, a stereo camera, a monocular camera, an infrared camera, and other cameras. The vehicle outside information detecting section 7420 includes, for example, at least one of an environment sensor that detects the current weather, and a surrounding information detecting sensor that detects another vehicle, an obstacle, a pedestrian, or the like around the vehicle including the vehicle control system 7000.

The environment sensor may be, for example, at least one of a raindrop sensor that detects rainy weather, a fog sensor that detects a fog, a sunshine sensor that detects the degree of sunshine, a snow sensor that detects a snowfall. The surrounding information detecting sensor may be at least one of an ultrasonic sensor, a radar apparatus, and a light detection and ranging/laser imaging detection and ranging (LIDAR) apparatus. These imaging section 7410 and vehicle outside information detecting section 7420 may be installed as independent sensors or apparatuses, or as an apparatus into which sensors and apparatuses are integrated.

FIG. 25 illustrates an example of installation positions of the imaging section 7410 and the vehicle outside information detecting section 7420. Imaging sections 7910, 7912, 7914, 7916, and 7918 are positioned, for example, at least one of the front nose, a side mirror, the rear bumper, the back door, and the upper part of the windshield in the vehicle compartment of a vehicle 7900. The imaging section 7910 attached to the front nose and the imaging section 7918 attached to the upper part of the windshield in the vehicle compartment chiefly acquire images of the area ahead of the vehicle 7900. The imaging sections 7912 and 7914 attached to the side mirrors chiefly acquire images of the areas on the sides of the vehicle 7900. The imaging section 7916 attached to the rear bumper or the back door chiefly acquires images of the area behind the vehicle 7900. The imaging section 7918 attached to the upper part of the windshield in the vehicle compartment is used chiefly to detect a preceding vehicle, a pedestrian, an obstacle, a traffic light, a traffic sign, a lane, or the like.

Note that FIG. 25 illustrates an example of the respective imaging ranges of the imaging sections 7910, 7912, 7914, and 7916. An imaging range a represents the imaging range of the imaging section 7910 attached to the front nose. Imaging ranges b and c respectively represent the imaging ranges of the imaging sections 7912 and 7914 attached to the side mirrors. An imaging range d represents the imaging range of the imaging section 7916 attached to the rear bumper or the back door. For example, overlaying image data captured by the imaging sections 7910, 7912, 7914, and 7916 offers an overhead image that looks down on the vehicle 7900.

Vehicle outside information detecting sections 7920, 7922, 7924, 7926, 7928, and 7930 attached to the front, the rear, the sides, the corners, and the upper part of the windshield in the vehicle compartment of the vehicle 7900 may be, for example, ultrasonic sensors or radar apparatuses. The vehicle outside information detecting sections 7920, 7926, and 7930 attached to the front nose, the rear bumper, the back door, and the upper part of the windshield in the vehicle compartment of the vehicle 7900 may be, for example, LIDAR apparatuses. These vehicle outside information detecting sections 7920 to 7930 are used chiefly to detect a preceding vehicle, a pedestrian, an obstacle, or the like.

The description will continue with reference to FIG. 24 again. The vehicle outside information detecting unit 7400 causes the imaging section 7410 to capture images of the outside of the vehicle, and receives the captured image data. Further, the vehicle outside information detecting unit 7400 receives detection information from the connected vehicle outside information detecting section 7420. In the case where the vehicle outside information detecting section 7420 is an ultrasonic sensor, a radar apparatus, or a LIDAR apparatus, the vehicle outside information detecting unit 7400 causes ultrasound, radio waves, or the like to be transmitted, and receives the information of the received reflected waves. The vehicle outside information detecting unit 7400 may perform processing of detecting an object such as a person, a car, an obstacle, a traffic sign, or a letter on a road, or processing of detecting the distance on the basis of the received information. The vehicle outside information detecting unit 7400 may perform environment recognition processing of recognizing a rainfall, a fog, a road condition, or the like on the basis of the received information. The vehicle outside information detecting unit 7400 may compute the distance to an object outside the vehicle on the basis of the received information.

Further, the vehicle outside information detecting unit 7400 may perform image recognition processing of recognizing a person, a car, an obstacle, a traffic sign, a letter on a road, or the like, or processing of detecting the distance on the basis of the received image data. The vehicle outside information detecting unit 7400 may perform distortion correcting processing, positioning processing, or the like on the received image data, and combine image data captured by a different imaging section 7410 to generate an overhead view or a panoramic image. The vehicle outside information detecting unit 7400 may use the image data captured by the other imaging section 7410 to perform viewpoint converting processing.

The vehicle inside information detecting unit 7500 detects information on the inside of the vehicle. The vehicle inside information detecting unit 7500 is connected, for example, to a driver state detecting section 7510 that detects the state of the driver. The driver state detecting section 7510 may include a camera that images the driver, a biological sensor that detects biological information of the driver, a microphone that picks up sounds in the vehicle compartment, or the like. The biological sensor is attached, for example, to a seating face, the steering wheel, or the like, and detects biological information of the passenger sitting on the seat or the driver gripping the steering wheel. The vehicle inside information detecting unit 7500 may compute the degree of the driver's tiredness or the degree of the driver's concentration or determine whether or not the driver have a doze, on the basis of detection information input from the driver state detecting section 7510. The vehicle inside information detecting unit 7500 may perform processing such as noise cancelling processing on the picked-up audio signal.

The integrated control unit 7600 controls the overall operation inside the vehicle control system 7000 in accordance with a variety of programs. The integrated control unit 7600 is connected to an input section 7800. The input section 7800 is implemented as an apparatus such as a touch panel, a button, a microphone, a switch, or a lever on which a passenger can perform an input operation. The integrated control unit 7600 may receive data obtained by recognizing the sound input through the microphone. The input section 7800 may be, for example, a remote control apparatus that uses infrared light or other radio waves, or an external connection apparatus such as a mobile telephone or a personal digital assistant (PDA) corresponding to the operation of the vehicle control system 7000. The input section 7800 may be, for example, a camera. In that case, a passenger can input information through gestures. Alternatively, data may be input that is obtained by detecting the movement of a wearable apparatus worn by a passenger. Moreover, the input section 7800 may include an input control circuit or the like that generates an input signal, for example, on the basis of information input by a passenger or the like using the above-described input section 7800, and outputs the generated input signal to the integrated control unit 7600. The passenger or the like operates this input section 7800, thereby inputting various kinds of data to the vehicle control system 7000 or instructing the vehicle control system 7000 about a processing operation.

The storage section 7690 may include a read only memory (ROM) that stores a variety of programs to be executed by a microcomputer, and a random access memory (RAM) that stores a variety of parameters, operation results, sensor values, or the like. Further, the storage section 7690 may be implemented as a magnetic storage device such as a hard disk drive (HDD), a semiconductor storage device, an optical storage device, a magneto-optical storage device, or the like.

The general-purpose communication I/F 7620 is a general-purpose communication I/F that mediates in communication between varieties of apparatuses in an external environment 7750. The general-purpose communication I/F 7620 may implement a cellular communication protocol such as Global System of Mobile communications (GSM (registered trademark)), WiMAX (registered trademark), Long Term Evolution (LTE (registered trademark)) or LTE-Advanced (LTE-A), or other wireless communication protocols such as a wireless LAN (which is also referred to as Wi-Fi (registered trademark)) or Bluetooth (registered trademark). The general-purpose communication I/F 7620 may be connected to an apparatus (such as an application server or a control server) on an external network (such as the Internet, a cloud network, or a network specific to a service provider), for example, via a base station or an access point. Further, the general-purpose communication I/F 7620 may be connected to a terminal (such as a terminal of the driver, a pedestrian or a store, or a machine type communication (MTC) terminal) in the vicinity of the vehicle, for example, using the peer-to-peer (P2P) technology.

The dedicated communication I/F 7630 is a communication I/F that supports a communication protocol defined for the purpose of use for vehicles. The dedicated communication I/F 7630 may implement a standard protocol such as wireless access in vehicle environment (WAVE), which is a combination of IEEE 802.11p for the lower layer and IEEE 1609 for the upper layer, dedicated short range communications (DSRC), or a cellular communication protocol. The dedicated communication I/F 7630 typically performs V2X communication. The V2X communication is a concept including one or more of vehicle-to-vehicle communication, vehicle-to-infrastructure communication, vehicle-to-home communication, and vehicle-to-pedestrian communication.

The positioning section 7640 receives, for example, global navigation satellite system (GNSS) signals (such as global positioning system (GPS) signals from a GPS satellite) from a GNSS satellite for positioning, and generates position information including the latitude, longitude, and altitude of the vehicle. Additionally, the positioning section 7640 may also identify the present position by exchanging signals with a wireless access point, or acquire position information from a terminal such as a mobile phone, a PHS, or a smartphone that has a positioning function.

The beacon receiving section 7650 receives radio waves or electromagnetic waves, for example, from a wireless station or the like installed on the road, and acquires information such as the present position, traffic congestion, closed roads, or necessary time. Additionally, the function of the beacon receiving section 7650 may be included in the above-described dedicated communication I/F 7630.

The onboard apparatus I/F 7660 is a communication interface that mediates in connections between the microcomputer 7610 and a variety of onboard apparatuses 7760 in the vehicle. The onboard apparatus I/F 7660 may use a wireless communication protocol such as a wireless LAN, Bluetooth (registered trademark), near field communication (NFC), or a wireless USB (WUSB) to establish a wireless connection. Further, the onboard apparatus I/F 7660 may also establish a wired connection such as a universal serial bus (USB), a high-definition multimedia interface (HDMI (registered trademark)), or a mobile high-definition link (MHL) via a connection terminal (not illustrated) (and a cable if necessary). The onboard apparatuses 7760 may include, for example, at least one of a mobile apparatus of a passenger, a wearable apparatus of a passenger, and an information apparatus carried into or attached to the vehicle. Further, the onboard apparatuses 7760 may also include a navigation apparatus that searches for routes to any destination. The onboard apparatus I/F 7660 exchanges control signals or data signals with these onboard apparatuses 7760.

The in-vehicle network I/F 7680 is an interface that mediates in communication between the microcomputer 7610 and the communication network 7010. The in-vehicle network I/F 7680 transmits and receives signals or the like in compliance with a predetermined protocol supported by the communication network 7010.

The microcomputer 7610 of the integrated control unit 7600 controls the vehicle control system 7000 in accordance with a variety of programs on the basis of information acquired via at least one of the general-purpose communication I/F 7620, the dedicated communication I/F 7630, the positioning section 7640, the beacon receiving section 7650, the onboard apparatus I/F 7660, and the in-vehicle network I/F 7680. For example, the microcomputer 7610 may calculate a control target value of the driving force generating apparatus, the steering mechanism, or the braking apparatus on the basis of acquired information on the inside and outside of the vehicle, and output a control instruction to the drive line control unit 7100. For example, the microcomputer 7610 may perform cooperative control for the purpose of executing the functions of an advanced driver assistance system (ADAS) including vehicle collision avoidance or impact reduction, follow-up driving based on the inter-vehicle distance, constant vehicle speed driving, vehicle collision warning, vehicle lane departure warning, or the like. Further, the microcomputer 7610 may control the driving force generating apparatus, the steering mechanism, the braking apparatus, or the like on the basis of acquired information on the areas around the vehicle, thereby performing cooperative control for the purpose of automatic driving or the like that allows the vehicle to autonomously travel irrespective of any operation of a driver.

The microcomputer 7610 may generate three-dimensional distance information on the distance between the vehicle and an object such as a nearby structure or person on the basis of information acquired via at least one of the general-purpose communication I/F 7620, the dedicated communication I/F 7630, the positioning section 7640, the beacon receiving section 7650, the onboard apparatus I/F 7660, and the in-vehicle network I/F 7680, and create local map information including surrounding information on the present position of the vehicle. Further, the microcomputer 7610 may predict danger such as vehicle collisions, approaching pedestrians or the like, or entry to closed roads on the basis of acquired information, and generate a warning signal. The warning signal may be, for example, a signal used to generate a warning sound or turn on the warning lamp.

The sound and image output section 7670 transmits an output signal of at least one of a sound and an image to an output apparatus capable of visually or aurally notifying a passenger of the vehicle or the outside of the vehicle of information. In the example of FIG. 24, an audio speaker 7710, a display section 7720, and an instrument panel 7730 are exemplified as the output apparatus. For example, the display section 7720 may include at least one of an onboard display and a head-up display. The display section 7720 may have an augmented reality (AR) display function. The output apparatus may also be an apparatus other than these apparatuses like a headphone, a wearable apparatus such as a glasses-type display worn by a passenger, a projector, or a lamp. In a case where the output apparatus is a display apparatus, the display apparatus visually displays a result obtained by the microcomputer 7610 performing various kinds of processing or information received from another control unit in a variety of forms such as text, images, tables, or graphs. Further, in a case where the output apparatus is a sound output apparatus, the sound output apparatus converts audio signals including reproduced sound data, acoustic data, or the like into analog signals, and aurally outputs the analog signals.

Note that, in the example illustrated in FIG. 24, at least two control units connected via the communication network 7010 may be integrated into one control unit. Alternatively, the individual control units may be configured as a plurality of control units. Moreover, the vehicle control system 7000 may also include another control unit that is not illustrated. Further, a part or the whole of the functions executed by any of the control units may be executed by another control unit in the above description. That is, as long as information is transmitted and received via the communication network 7010, predetermined operation processing may be performed by any of the control units. Similarly, a sensor or an apparatus connected to any of the control units may be connected to another control unit, and the control units may transmit and receive detection information to and from each other via the communication network 7010.

Note that a computer program for implementing each function of the streaming reception apparatus 30 according to the present embodiment described with reference to FIG. 6 can be implemented in any control unit or the like. In addition, there can also be provided a computer-readable recording medium having such a computer program stored therein. Examples of the recording medium include a magnetic disk, an optical disc, a magneto-optical disk, a flash memory, and the like. In addition, the computer program may also be distributed via a network, for example, using no recording medium.

In the above-described vehicle control system 7000, the streaming reception apparatus 30 according to the present embodiment described with reference to FIG. 6 can be applied to the integrated control unit 7600 according to the application example illustrated in FIG. 24. For example, the imaging section 7410 may correspond to the streaming transmission apparatus 20. The display section 7720 or the electronic mirror may correspond to the display apparatus 40. The integrated control unit 7600 may have the function of the streaming reception apparatus 30. In this case, a main streaming transmission start request may be transmitted to the imaging section 7410 designated by a user. Alternatively, a main streaming transmission start request may be transmitted to the imaging section 7410 corresponding to sensing information. For example, a main streaming transmission start request may be transmitted to the imaging section 7410 that images a site where a proximity sensor detects proximity to another object. Alternatively, in accordance with the gear state of a vehicle, for example, in the case where the gear is set at the back gear, a main streaming transmission start request may be transmitted to the imaging section 7410 that images the area behind the vehicle.

In addition, at least some components of the streaming reception apparatus 30 described with reference to FIG. 6 may be implemented as a module (e.g., integrated circuit module including one die) for the integrated control unit 7600 illustrated in FIG. 24. Alternatively, the streaming reception apparatus 30 described with reference to FIG. 6 may be implemented as the plurality of control units of the vehicle control system 7000 illustrated in FIG. 24.

7. Conclusion

According to an embodiment of the present disclosure as described above, each streaming transmission apparatus 20 transmits sub-streaming, and the streaming transmission apparatus 20 that receives a main streaming transmission start request further transmits main streaming. This configuration makes it possible to suppress the amount of consumed network bands as compared with the case where all the streaming transmission apparatuses 20 transmit main streaming. In addition, the streaming reception apparatus 30 can obtain a sub-video from sub-streaming with no resizing, so that it is also possible to reduce the processing load on the streaming reception apparatus 30.

In addition, according to an embodiment of the present disclosure, the streaming transmission apparatus 20 that receives a main streaming transmission start request concurrently transmit both main streaming and sub-streaming. Therefore, the streaming reception apparatus 30 can display a main video on the basis of the main streaming transmitted from the streaming transmission apparatus 20 that receives a main streaming transmission start request, and display a sub-video on the basis of the sub-streaming in parallel.

It should be understood by those skilled in the art that various modifications, combinations, sub-combinations and alterations may occur depending on design requirements and other factors insofar as they are within the scope of the appended claims or the equivalents thereof.

For example, the respective steps of the processing of the streaming transmission apparatus 20 and the streaming reception apparatus 30 in the present specification do not necessarily have to be chronologically processed in the order described as the sequence diagrams or the flowcharts. For example, the respective steps in the processing executed by the streaming transmission apparatus 20 and the streaming reception apparatus 30 may be performed in order different from the order described in the flowcharts, or may be performed in parallel.

In addition, it is also possible to manufacture a computer program that allows the hardware such as CPUs, ROMs, and RAMs built in the streaming transmission apparatus 20 and the streaming reception apparatus 30 to perform the functions which are equivalent to those of the respective components of the streaming transmission apparatus 20 and the streaming reception apparatus 30 described above. There is also provided a storage medium having the computer program stored therein.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)
A reception apparatus comprising:
communication circuitry configured to transmit a first start request to a first streaming apparatus, the first start request is an instruction that orders the first streaming apparatus to commence transmitting first main streaming,
wherein the communication circuitry is configured to receive the first main streaming from the first streaming apparatus concurrently with first sub streaming from the first streaming apparatus.

(2)
The reception apparatus according to (1), wherein the communication circuitry is configured to transmit the first start request after receiving the first sub streaming.

(3)
The reception apparatus according to (1), wherein the communication circuitry is configured to transmit a stop request to the first streaming apparatus, the stop request is an instruction that orders the first streaming apparatus to stop transmitting the first main streaming.

(4)
The reception apparatus according to (1), wherein the first sub streaming and the first main streaming are generated from an image acquired by the first streaming apparatus, the first main streaming has a higher bit rate than a bit rate of the sub streaming.

(5)
The reception apparatus according to (1), wherein the communication circuitry is configured to receive second sub streaming from a second streaming apparatus, the second sub streaming is generated from an image acquired by the second streaming apparatus.

(6)
The reception apparatus according to (5), wherein the communication circuitry is configured to transmit a second start request to the second streaming apparatus in a manner that orders the second streaming apparatus to commence transmitting second main streaming, the second main streaming is generated from the image acquired by the second streaming apparatus and has a higher bit rate than a bit rate of the second sub streaming.

(7)

The reception apparatus according to (6), wherein the communication circuitry is configured to transmit a stop request to the first streaming apparatus, the stop request is an instruction that instructs the first streaming apparatus to stop transmitting the first main streaming prior to a transmission of the second start request from the communication circuitry.

(8)

The reception apparatus according to (5), wherein the communication circuitry is configured to transmit a designating request to the second streaming apparatus, the designating request is an instruction that orders the second streaming apparatus to commence outputting second main streaming and designates image data regarding to the second sub streaming as a main image to be outputted.

(9)

The reception apparatus according to (8), wherein the communication circuitry is configured to transmit a stop request to the first streaming apparatus after switching the first main streaming to the second main streaming, the stop request is an instruction that instructs the first streaming apparatus to stop transmitting the first main streaming.

(10)

The reception apparatus according to (1), further comprising:
display output circuitry configured to cause a screen to display first sub-video on a portion of the screen while simultaneously displaying first main video on a different portion of the screen, the display output circuitry is configured to generate the first sub-video from the first sub streaming and generate the first main video from the first main streaming.

(11)

A reception method comprising:
receiving, by communication circuitry, first sub streaming from a first streaming apparatus, and thereafter;
transmitting, from the communication circuitry to the first streaming apparatus, a start request orders the first streaming apparatus to commence transmitting first main streaming.

(12)

The reception method according to (11), further comprising:
transmitting, from the communication circuitry, a designating request after the communication circuitry receives the first main streaming from the first streaming apparatus, the designating request is an instruction that designates image data from a second streaming apparatus as a main image to be outputted and instructs the second streaming apparatus to commence transmitting second main streaming,
wherein the first streaming apparatus and the second streaming apparatus are from a plurality of streaming apparatuses.

(13)

The reception method according to (12), further comprising:
transmitting, from the communication circuitry, a stop request after switching as the main image from the first main streaming to the second main streaming, the stop request is an instruction that orders the first streaming apparatus to stop transmitting the first main streaming.

(14)

A streaming apparatus comprising:
communication circuitry configured to transmit sub streaming to a reception apparatus concurrently with transmitting main streaming to the reception apparatus.

(15)

The streaming apparatus according to (14), wherein the streaming apparatus is configured to transmit the main streaming to the reception apparatus as a result of receiving a start request from the reception apparatus.

(16)

The streaming apparatus according to (15), wherein the streaming apparatus is configured to inhibit transmitting the main streaming to the reception apparatus until the streaming apparatus receives the start request from the reception apparatus.

(17)

An operating room system comprising:
cameras configured to acquire image data; and
an audiovisual controller configured to:
receive a plurality of sub streaming from the cameras;
transmit a start request, the request is an instruction that orders one of the cameras to commence outputting main streaming; and
receive the main streaming concurrently with receiving the plurality of sub streaming,
wherein the main streaming has a higher bit rate than a bit rate for each of the plurality of sub streaming.

(18)

The operating room system according to (17), wherein the audiovisual controller is configured to use sensing information of a patient as a basis for selecting the one of the cameras to which the start request is transmitted.

(19)

A vehicle control system comprising:
cameras mounted onto a vehicle;
an integrated unit configured to:
receive a plurality of sub streaming from the cameras;
transmit a start request, the request is an instruction that orders one of the cameras to
commence outputting main streaming; and
receive the main streaming concurrently with receiving the plurality of sub streaming,
wherein the main streaming has a higher bit rate than a bit rate of each of the plurality of sub streaming.

(20)

The vehicle control system according to (19), further comprising:
a sensor configured to detect information regarding a relative position of the vehicle to an object that is outside of the vehicle, the integrated unit is configured to use the information as a basis for selecting the one of the cameras to which the start request is transmitted.

REFERENCE SIGNS LIST

12 hub
20 streaming transmission apparatus
30 streaming reception apparatus
40 display apparatus
42 display section
220 signal acquisition section
224 low-quality data generation section
228 sub-streaming generation section
232 high-quality data generation section
236 main streaming generation section
240 transmission control section
244 communication section
320 output control section 324 low-quality data decoding section
328 sub-streaming decoding section
332 high-quality data decoding section
336 main streaming decoding section
344 communication section
352 operation section
356 main streaming request section

What is claimed is:

1. A reception method comprising:
receiving, with communication circuitry, a first individual video stream of decoded low-quality video data at a first bit rate from a streaming apparatus prior to receiving a second individual video stream of decoded high-quality video data, wherein the first individual video stream is based on two or more sub-streaming video streams from a plurality of cameras, and wherein the second individual video stream is based on a main streaming video stream from only one video stream of the plurality of cameras;
transmitting, with the communication circuitry, a start request that requests the streaming apparatus to commence transmitting the second individual video stream in response to receiving the first individual video stream; and
displaying, with display output circuitry, the first individual video stream on a first portion of a screen while simultaneously displaying the second individual video stream on a second portion of the screen that is different from the first portion,
wherein
the first portion has a first display size,
the second portion has a second display size, and
the first display size is equal to the second display size.

2. The reception method according to claim 1, further comprising:
receiving, with the communication circuitry, the first individual video stream concurrently with the second individual video stream, wherein the second individual video stream has a second bit rate that differs from the first bit rate.

3. The reception method according to claim 2, wherein the second bit rate is higher than the first bit rate.

4. The reception method according to claim 1, further comprising:
transmitting, with the communication circuitry, a stop request that requests the streaming apparatus to stop transmitting the second individual video stream.

5. The reception method according to claim 4, further comprising:
transmitting, with the communication circuitry, an additional start request that requests an additional streaming apparatus to commence transmitting a third individual video stream.

6. The reception method according to claim 5, further comprising:
transmitting, with the communication circuitry, the stop request before the communication circuitry transmits the additional start request.

7. The reception method according to claim 5, further comprising:
transmitting, with the communication circuitry, the stop request after a display output circuitry switches from the second individual video stream to the third individual video stream.

8. A reception apparatus comprising:
communication circuitry configured to:
receive a first individual video stream of decoded low-quality video data at a first bit rate from a streaming apparatus prior to receiving a second individual video stream of decoded high-quality video data from the streaming apparatus, wherein the first individual video stream is based on two or more sub-streaming video streams from a plurality of cameras, and wherein the second individual video stream is based on a main streaming video stream from only one of the plurality of cameras, and
transmit a start request that requests the streaming apparatus to commence transmitting the second individual video stream; and
output circuitry configured to:
output the first individual video stream, and
output the second individual video stream,
wherein the communication circuitry receives the second individual video stream only after transmitting the start request,
wherein the output circuitry further includes
display output circuitry configured to display the first individual video stream on a first portion of a screen while causing the screen to simultaneously display the second individual video stream on a second portion of the screen that is different from the first portion, and
wherein
the first portion has a first display size,
the second portion has a second display size, and
the first display size is equal to the second display size.

9. The reception apparatus according to claim 8, wherein the communication circuitry is configured to:
receive, from the streaming apparatus concurrently with the communication circuitry receiving the first individual video stream, the second individual video stream at a second bit rate that differs from the first bit rate.

10. The reception apparatus according to claim 9, wherein the second bit rate is higher than the first bit rate.

11. The reception apparatus according to claim 8, wherein the communication circuitry is configured to:
transmit, to the streaming apparatus when the communication circuitry receives the second individual video stream, a stop request that orders the streaming apparatus to stop transmitting the second individual video stream.

12. The reception apparatus according to claim 11, wherein the communication circuitry is configured to:
transmit, to an additional streaming apparatus, an additional start request that orders the additional streaming apparatus to commence transmitting a third individual video stream.

13. The reception apparatus according to claim 12, wherein the communication circuitry is configured to:
transmit the stop request to the streaming apparatus before the communication circuitry transmits the additional start request to the additional streaming apparatus.

14. The reception apparatus according to claim 12, wherein the communication circuitry is configured to:
transmit the stop request to the streaming apparatus after the reception apparatus switches from the second individual video stream to the third individual video stream.

15. A vehicle control system comprising:
a plurality of cameras mounted onto a vehicle;
a sensor configured to:
detect information regarding a relative position of the vehicle to an object that is outside of the vehicle; and an integrated circuitry configured to:
> receive a plurality of sub streaming from the plurality of cameras,
> select one of the plurality of cameras based on the information,
> transmit a start request to the one of the plurality of cameras that is selected, the start request is an instruction that orders the one of the plurality of cameras to commence outputting main streaming,
> receive the main streaming, and
> control a display to display the main streaming concurrently with the plurality of sub streaming.

16. The vehicle control system according to claim 15, wherein a first camera of the plurality of cameras has a first field-of-view including a first object, wherein a second camera of the plurality of cameras has a second field-of-view including a second object, wherein the first field-of-view does not include the second object, wherein the second field-of-view does not include the first object, and wherein one of the first object or the second object is the object.

17. The vehicle control system according to claim 15, wherein the plurality of sub streaming is received concurrently with the main streaming, wherein each of the plurality of sub streaming has a first bit rate, and wherein the main streaming has a second bit rate that differs from the first bit rate.

18. The vehicle control system according to claim 17, wherein the second bit rate is higher than the first bit rate.

19. The vehicle control system according to claim 15, wherein the integrated circuitry is further configured to:
> transmit a stop request that requests an end to transmission of the main streaming.

20. The vehicle control system according to claim 19, wherein the integrated circuitry is further configured to:
> transmit an additional start request that requests a commencement of a transmission of a second main streaming.

21. The vehicle control system according to claim 20, wherein the integrated circuitry is further configured to:
> transmit the stop request before the transmission of the additional start request.

22. The vehicle control system according to claim 20, wherein the integrated circuitry is further configured to:
> transmit the stop request after switching from the main streaming to the second main streaming.

* * * * *